US012751948B2

(12) United States Patent
Badawy et al.

(10) Patent No.: US 12,751,948 B2
(45) Date of Patent: *Oct. 6, 2026

(54) DOSAGE FORMS FOR TYK2 INHIBITORS

(71) Applicant: Bristol-Myers Squibb Company, Princeton, NJ (US)

(72) Inventors: Sherif Ibrahim Farag Badawy, Dayton, NJ (US); Jonathan R. Brown, Chester (GB); Candice Y. Choi, Palisades Park, NJ (US); Christoph Gesenberg, Cheshire, CT (US); Vivienne Gray, Barnston (GB); John Wynne Jones, Mwynglawdd (GB); Umesh Kestur, North Brunswick, NJ (US); Balvinder S. Vig, Milltown, NJ (US); Xiaotian S. Yin, Kendall Park, NJ (US); Christopher A. Zordan, East Brunswick, NJ (US); Corey Bloom, Bend, OR (US); Ian Yates, Bend, OR (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/406,921

(22) Filed: Dec. 2, 2025

(65) Prior Publication Data

US 2026/0083733 A1 Mar. 26, 2026

Related U.S. Application Data

(63) Continuation of application No. 17/639,481, filed as application No. PCT/US2020/051342 on Sep. 18, 2020, now Pat. No. 12,521,390.

(60) Provisional application No. 62/902,218, filed on Sep. 18, 2019.

(51) Int. Cl.

| | |
|---|---|
| ***A61K 31/501*** | (2006.01) |
| ***A61K 9/00*** | (2006.01) |
| ***A61K 9/20*** | (2006.01) |
| ***A61K 9/28*** | (2006.01) |
| ***A61K 45/06*** | (2006.01) |

(52) U.S. Cl.

CPC .......... *A61K 31/501* (2013.01); *A61K 9/0053* (2013.01); *A61K 9/2009* (2013.01); *A61K 9/2013* (2013.01); *A61K 9/2018* (2013.01); *A61K 9/2054* (2013.01); *A61K 9/284* (2013.01); *A61K 45/06* (2013.01)

(58) Field of Classification Search

CPC .. A61K 31/501; A61K 9/0053; A61K 9/2009; A61K 9/2013; A61K 9/2018; A61K 9/2054; A61K 9/284; A61K 45/06

See application file for complete search history.

(56) References Cited

U.S. PATENT DOCUMENTS

| | | | |
|---|---|---|---|
| 6,706,283 B1 | 3/2004 | Appel et al. | |
| RE47,929 E | 4/2020 | Moslin et al. | |
| 12,521,390 B2 * | 1/2026 | Badawy | A61K 9/1652 |
| 2002/0015731 A1 | 2/2002 | Appel et al. | |
| 2003/0198674 A1 | 10/2003 | Curatolo et al. | |
| 2009/0011018 A1 | 1/2009 | Kondo et al. | |
| 2012/0087978 A1 | 4/2012 | Nause | |
| 2014/0107107 A1 | 4/2014 | Gautschl et al. | |
| 2015/0024054 A1 | 1/2015 | Curatolo et al. | |
| 2016/0015628 A1 | 1/2016 | Caldwell | |
| 2018/0193347 A1 | 7/2018 | Herbig et al. | |
| 2023/0255964 A1 | 8/2023 | Badawy et al. | |
| 2024/0325388 A1 | 10/2024 | Kestur et al. | |

FOREIGN PATENT DOCUMENTS

| | | |
|---|---|---|
| CN | 101152158 A | 4/2008 |
| EP | 0901786 A2 | 3/1999 |

(Continued)

OTHER PUBLICATIONS

Burke et al., Autoimmune pathways in mice and humans are blocked by pharmacological stabilization of the TYK2 pseudokinase domain, *Science Translational Medicine*, vol. 1, No. 502, Jul. 24, 2019, pp. 1-16.

(Continued)

*Primary Examiner* — Andrew D Kosar
*Assistant Examiner* — Phillip Matthew Rzeczycki
(74) *Attorney, Agent, or Firm* — Covington & Burling LLP; Jennifer L. Robbins; Melody Wu

(57) ABSTRACT

Stable and bioavailable formulations and dosage forms comprising a dispersion (e.g., spray-dried dispersion) of solid amorphous 6-(cyclopropaneamido)-4-((2-methoxy-3-(1-methyl-1H-1,2,4-triazol-3-yl)phenyl)amino)-N-(methyl-d3)pyridazine-3-carboxamide (Formula (I); BMS-986165) in a solid polymer matrix are provided for the treatment of auto-immune and auto-inflammatory diseases such as an inflammatory bowel disease (IBD) and psoriasis:

Formula (I)

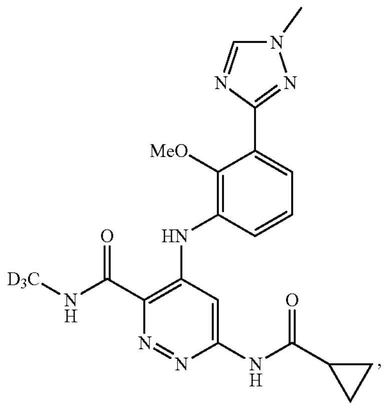

29 Claims, 14 Drawing Sheets

(56) References Cited

FOREIGN PATENT DOCUMENTS

| | | | |
|---|---|---|---|
| EP | 1027885 | A2 | 8/2000 |
| EP | 1027887 | A2 | 8/2000 |
| EP | 1027888 | A2 | 8/2000 |
| WO | WO-2014/043208 | A1 | 3/2014 |
| WO | WO-2014/074661 | A1 | 5/2014 |
| WO | WO-2019/246273 | A1 | 12/2019 |
| WO | WO-2022/061149 | A1 | 3/2022 |

OTHER PUBLICATIONS

Friesen et al., Hydroxypropyl Methylcellulose Acetate Succinate-Based Spray-Dried Dispersions: An Overview, *Molecular Pharmaceutics*, vol. 5, No. 6, Dec. 1, 2008, pp. 1003-1019.

Wrobleski et al., Highly Selective Inhibition of Tyrosine Kinase 2 (TYK2) for the Treatment of Autoimmune Diseases: Discovery of the Allosteric Inhibitor BMS-986165, *J. Med. Chem.*, vol. 62, Jul. 18, 2019, pp. 8973-8995, XP055629848, ISSN: 0022-2623, DOI: 10.1021/acs.jmedchem.9b00444.

Curatolo et al., Utility of Hydroxypropylmethylcellulose Acetate Succinate (HPMCAS) for Initiation and Maintenance of Drug Supersaturation in the GI Milieu, *Pharmaceutical Research*, vol. 26, No. 6, pp. 1419-1431 (Jun. 2009).

International Search Report and Written Opinion for PCT/US2020/051342 dated Dec. 10, 2020.

Savjani et al., Drug Solubility: Importance and Enhancement Techniques, International Scholarly Research Network ISRN Pharmaceutics, vol. 2012, Article ID 195727, pp. 1-10 (2012).

Papp et al., Phase 2 Trial of Selective Tyrosine Kinase 2 Inhibition in Psoriasis, New England Journal of Medicine, vol. 379(14), pp. 1313-1321 (2018).

Tajarobi et al., The influence of crystallization inhibition of HPMC and HPMCAS on model substance dissolution and release in swellable matrix tablets, European Journal of Pharmaceutics and Biopharmaceutics, vol. 78, pp. 125-133 (2011).

Third Party Observations filed for EP4031110 (EP Appln. No. 20781719.8), 4 pages, dated Jan. 30, 2024.

Examining Division Communication for EP4031110 (EP Appln. No. 20781719.8), 8 pages, dated May 3, 2024.

Applicant Response to Examiner for EP4031110 (EP Appln. No. 20781719.8), 27 pages, dated Sep. 2, 2024.

Rusinol et al., Tyk2 Targeting in Immune-Mediated Inflammatory Diseases, *International Journal of Molecular Sciences*, 2023, 24, 3391 (Year: 2023).

Ramakrishna et al., Tyrosine kinse 2 inhibitors in autoimmune diseases, *Autoimmunity Reviews*, 23 (2024), 103649 (Year: 2024).

Burke et al., Selective Inhibition of Tyrosine Kinase 2 (TYK2) with BMS-986165 is Efficacious in IL-23-Mediated Diseases: Evidence from Preclinical IBD Models and from a Psoriasis Study, American Journal of Gastroenterology, 113; Abstracts S355, Oct. 2018 (Year: 2018).

FDA's Global Substance Registration System Unique Ingredient Identifier (UNII) search page (https://precision.fda.gov/uniisearch), and record for UNII NX76LV5T8J, Methylacrylic Acid and Ethyl Acrylate Copolymer (https://precision.fda.gov/uniisearch/srs/unii/NX76LV5T8J), accessed Mar. 2026.

Pandi et al., Amorphous solid dispersions: An update for preparation, characterization, mechanism on bioavailability, stability, regulatory considerations and marketed products. International Journal of Pharmaceutics, vol. 586: 119560 (2020).

Tonglairoum et al., Effect of polyethylene glycol on cellulose acetate films designed for controlled porosity osmotic pump systems. Indian Journal of Pharmaceutical Sciences 81(1): 117-123 (2019).

Leuner, C. et al., Improving drug solubility for oral delivery using solid dispersions, *European Journal of Pharmaceutics and Biopharmaceutics*, vol. 50, No. 1, pp. 47-60 (2000).

Wang, Xue-Qing et al., pH-sensitive polymeric nanoparticles to improve oral bioavailability of peptide/protein drugs and poorly water-soluble drugs, *European Journal of Pharmaceutics and Biopharmaceutics*, vol. 82, No. 2, pp. 219-229 (2012).

Kim, Hyuk Il et al., Swelling and drug release behavior of tablets coated with aqueous hydroxypropyl methylcellulose phthalate (HPMCP) nanoparticles, *Journal of Controlled Release*, vol. 89, No. 2, pp. 225-233 (2003).

Patra, Ch. Niranjan et al., Pharmaceutical significance of Eudragit: A review, *Future Journal of Pharmaceutical Sciences*, vol. 3, No. 1, pp. 33-45 (2017).

Zahirul, Khan M. et al., A pH-Dependent Colon-Targeted Oral Drug Delivery System Using Methacrylic Acid Copolymers. II. Manipulation of Drug Release Using Eudragit L100 and Eudragit S100 Combinations, *Drug Development and Industrial Pharmacy*, vol. 26, No. 5, pp. 549-554 (2000).

* cited by examiner

DOSAGE FORMS FOR TYK2 INHIBITORS

CROSS-REFERENCE TO RELATED APPLICATIONS

This application is a continuation of U.S. application Ser. No. 17/639,481, filed on Mar. 1, 2022, which is a national stage application of International Application No. PCT/US2020/051342, filed on Sep. 18, 2020, which claims priority to U.S. Provisional Application No. 62/902,218, filed on Sep. 19, 2019; the entire contents of each of the foregoing applications are hereby incorporated by reference herein.

FIELD OF THE INVENTION

The present invention relates to dosage forms and formulations of 6-(cyclopropaneamido)-4-((2-methoxy-3-(1-methyl-1H-1,2,4-triazol-3-yl)phenyl)amino)-N-(methyl-d3) pyridazine-3-carboxamide, a highly selective inhibitor of Tyk2. The formulations and dosage forms provide for the bioavailability of 6-(cyclopropaneamido)-4-((2-methoxy-3-(1-methyl-1H-1,2,4-triazol-3-yl)phenyl)amino)-N-(methyl-d3)pyridazine-3-carboxamide, while exhibiting acceptable physical and chemical stability, and may be used for the treatment of auto-immune and auto-inflammatory diseases such as an inflammatory bowel disease (IBD) and psoriasis.

BACKGROUND OF THE INVENTION

Tyrosine kinase 2 (Tyk2) is a member of the Janus kinase (JAK) family of nonreceptor tyrosine kinases and has been shown to be critical in regulating the signal transduction cascade downstream of receptors for IL-12, IL-23, and type I interferons in both mice (Ishizaki, M et al., "Involvement of tyrosine kinase-2 in both the IL-12/Th1 and IL-23/Th17 axes in vivo," J. Immunol., 187:181-189 (2011); Prchal-Murphy, M. et al., "TYK2 kinase activity is required for functional type I interferon responses in vivo," PLoS One, 7:e39141 (2012)) and humans (Minegishi, Y. et al., "Human tyrosine kinase 2 deficiency reveals its requisite roles in multiple cytokine signals involved in innate and acquired immunity," Immunity, 25:745-755 (2006)). Tyk2 mediates the receptor-induced phosphorylation of members of the STAT family of transcription factors, an essential signal that leads to the dimerization of STAT proteins and the transcription of STAT-dependent pro-inflammatory genes. Tyk2-deficient mice are resistant to experimental models of colitis, psoriasis, and multiple sclerosis, demonstrating the importance of Tyk2-mediated signaling in autoimmunity and related disorders (Ishizaki, M. et al., "Involvement of tyrosine kinase-2 in both the IL-12/Th1 and IL-23/Th17 axes in vivo," J. Immunol., 187:181-189 (2011); Oyamada, A. et al., "Tyrosine kinase 2 plays critical roles in the pathogenic CD4 T cell responses for the development of experimental autoimmune encephalomyelitis," J. Immunol., 183:7539-7546 (2009)).

In humans, individuals expressing an inactive variant of Tyk2 are protected from multiple sclerosis and possibly other autoimmune disorders (Couturier, N. et al., "Tyrosine kinase 2 variant influences T lymphocyte polarization and multiple sclerosis susceptibility," Brain, 134:693-703 (2011)). Genome-wide association studies have shown other variants of Tyk2 to be associated with autoimmune disorders such as Crohn's disease, psoriasis, systemic lupus erythematosus, and rheumatoid arthritis, further demonstrating the importance of Tyk2 in autoimmunity (Ellinghaus, D. et al., "Combined Analysis of Genome-wide Association Studies for Crohn Disease and Psoriasis Identifies Seven Shared Susceptibility Loci," Am. J. Hum. Genet., 90:636-647 (2012); Graham, D. et al., "Association of polymorphisms across the tyrosine kinase gene, TYK2 in UK SLE families," Rheumatology (Oxford), 46:927-930 (2007); Eyre, S. et al., "High-density genetic mapping identifies new susceptibility loci for rheumatoid arthritis," Nat. Genet., 44:1336-1340 (2012)).

BMS-986165 refers to a compound of the following Formula (I)

Formula (I)

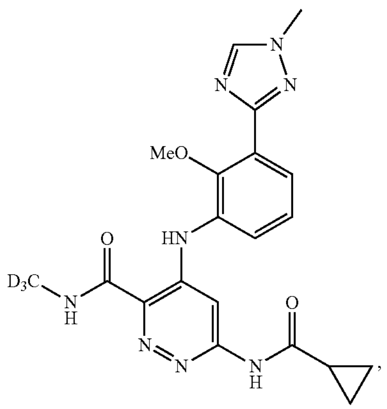

which is 6-(cyclopropaneamido)-4-((2-methoxy-3-(1-methyl-1H-1,2,4-triazol-3-yl)phenyl)amino)-N-(methyl-d3) pyridazine-3-carboxamide. BMS-986165, which is under investigation for the treatment of auto-immune and auto-inflammatory diseases such as psoriasis, psoriatic arthritis, lupus, lupus nephritis, Sjögren's syndrome, inflammatory bowel diseases (including ulcerative colitis and Crohn's disease), and ankylosing spondylitis, is a highly selective inhibitor of Tyk2-mediated signal transduction. It selectively binds to the Tyk2 pseudokinase (JH2) domain and blocks receptor-mediated Tyk2 activation by stabilizing the regulatory JH2 domain.

BMS-986165 and other amide-substituted heterocyclic compounds useful as modulators of IL-12, IL-23, and/or IFNα responses, methods of making the same, and methods of using the same are disclosed in U.S. Pat. No. 9,505,748 B2, the contents of which are hereby incorporated by reference in their entirety herein. Other methods of synthesizing BMS-986165 are disclosed in U.S. Provisional Patent Application No. 62/478,789 and PCT/US2018/025100 (published as WO 2018/183649), the contents of each of which are hereby incorporated by reference in their entirety herein.

BMS-986165 has been synthesized in a crystalline form, such as in crystalline Form A as is disclosed in U.S. Provisional Patent Application No. 62/478,789 and PCT/US2018/025114 (published as WO 2018/183656), the contents of each of which are hereby incorporated by reference in their entirety herein, in crystalline Form B as is disclosed in U.S. Provisional Patent Application No. 62/678,451 and PCT/US2019/034534 (published as WO 2019/232138), the contents of each of which are hereby incorporated by reference in their entirety herein, and in crystalline Form C and in crystalline Form D, as is disclosed in U.S. Provisional Patent Application No. 62/860,439 and PCT/US2020/036727, the contents of each of which are hereby incorporated by reference in their entirety herein.

Designing suitable formulations and dosage forms for BMS-986165 has presented several challenges, as efforts to design formulations that provide for bioavailability of the compound following oral administration, and that are also sufficiently stable upon storage, have not been successful.

Thus, there is a need in the art for formulations and dosage forms of 6-(cyclopropaneamido)-4-((2-methoxy-3-(1-methyl-1H-1,2,4-triazol-3-yl)phenyl)amino)-N-(methyl-d3) pyridazine-3-carboxamide (BMS-986165) that provide sufficient bioavailability for BMS-986165 while also providing sufficient stability of BMS-986165 upon storage. In particular, there is a need for formulations and dosage forms that provide for bioavailability of 6-(cyclopropaneamido)-4-((2-methoxy-3-(1-methyl-1H-1,2,4-triazol-3-yl)phenyl)amino)-N-(methyl-d3)pyridazine-3-carboxamide (BMS-986165) when BMS-986165 is co-administered with medication that raises gastric pH (e.g., medications such as antacids, H2 receptor antagonists, and/or proton pump inhibitors). In addition, and particularly when it is desirable to have extended-release of BMS-986165 following oral administration, there is a need for formulations and dosage forms that provide for bioavailability of 6-(cyclopropaneamido)-4-((2-methoxy-3-(1-methyl-1H-1,2,4-triazol-3-yl)phenyl) amino)-N-(methyl-d3)pyridazine-3-carboxamide (BMS-986165) in regions of the gastrointestinal tract (GI tract) such as the colon where water availability is low and/or where no bile salts are present to enhance solubility of the drug. At the same time, such formulations and dosage forms must provide sufficient stability of 6-(cyclopropaneamido)-4-((2-methoxy-3-(1-methyl-1H-1,2,4-triazol-3-yl)phenyl) amino)-N-(methyl-d3)pyridazine-3-carboxamide upon storage. The formulations and dosage forms of the present invention address these and other needs.

SUMMARY OF THE INVENTION

The present invention provides formulations of solid amorphous BMS-986165 that are physically and chemically stable, and that can be used to make oral dosage forms that provide for the bioavailability of BMS-986165. The formulations comprise amorphous BMS-986165 free base and one or more polymers. The formulations provide for the bioavailability of BMS-986165, including when administered to patients that have taken agents that raise gastric pH. Under such gastric pH-elevated conditions, dosage forms containing the formulations described herein exhibit bioavailability that is comparable to the bioavailability provided by crystalline BMS-986165 HCl salt capsule or by BMS-986165 free base in oral solution. The formulations further demonstrate superior stability; for example, the BMS-986165 HCl salt capsule requires refrigeration to prevent conversion of the salt to the free base form upon storage, whereas the solid amorphous BMS-986165 formulations and dosage forms exhibit physical stability upon storage under room temperature conditions. The formulations described herein are also suitable for making immediate release and modified release dosage forms.

Thus, certain embodiments of the present invention provide formulations and dosage forms comprising a solid dispersion of amorphous 6-(cyclopropaneamido)-4-((2-methoxy-3-(1-methyl-1H-1,2,4-triazol-3-yl)phenyl)amino)-N-(methyl-d3)pyridazine-3-carboxamide (BMS-986165). The formulations and dosage forms provide release and dissolution of BMS-986165 to a sufficient degree, and at a sufficiently fast rate, in media simulating the in vivo conditions of the gastrointestinal tract such that they are suitable for use as immediate release formulations and dosage forms. Such immediate release formulations may then be modified to provide controlled-release oral dosage forms of BMS-986165.

Embodiments of the present invention also provide extended release formulations that can be dosed to a patient once a day and provide a pharmacokinetic profile for BMS-986165 that is comparable to or is better than the pharmacokinetic profile for BMS-986165 provided by the immediate release tablet dosed twice a day. The extended release formulations as described herein provide for bioavailability of BMS-986165 in regions of the GI tract such as the colon where water availability is low and/or where no bile salts are present to enhance solubility of the drug. Such formulations would be especially helpful, for example, in the treatment of inflammatory bowel diseases such as ulcerative colitis and Crohn's disease. With the extended release BMS-986165 tablet formulations as described herein, patient compliance can be improved, and convenience to the patient and/or a caregiver is also improved, since only one tablet is dosed daily to the patient.

BRIEF DESCRIPTION OF THE DRAWINGS

FIG. 1A—initial; FIG. 1B—after 6 months of storage at 40° C./75% RH open.

FIG. 2A—initial; FIG. 2B—after 6 months of storage at 40° C./75% RH closed; FIG. 2C—after 6 months of storage at 40° C./75% RH open.

FIG. 3A—initial; FIG. 3B—after 6 months of storage at 40° C./75% RH closed; FIG. 3C—after 6 months of storage at 40° C./75% RH open.

FIG. 4A—initial; FIG. 4B—after 6 months of storage at 40° C./75% RH closed; FIG. 4C—after 6 months of storage at 40° C./75% RH open.

DETAILED DESCRIPTION OF THE INVENTION

Figure 1A:
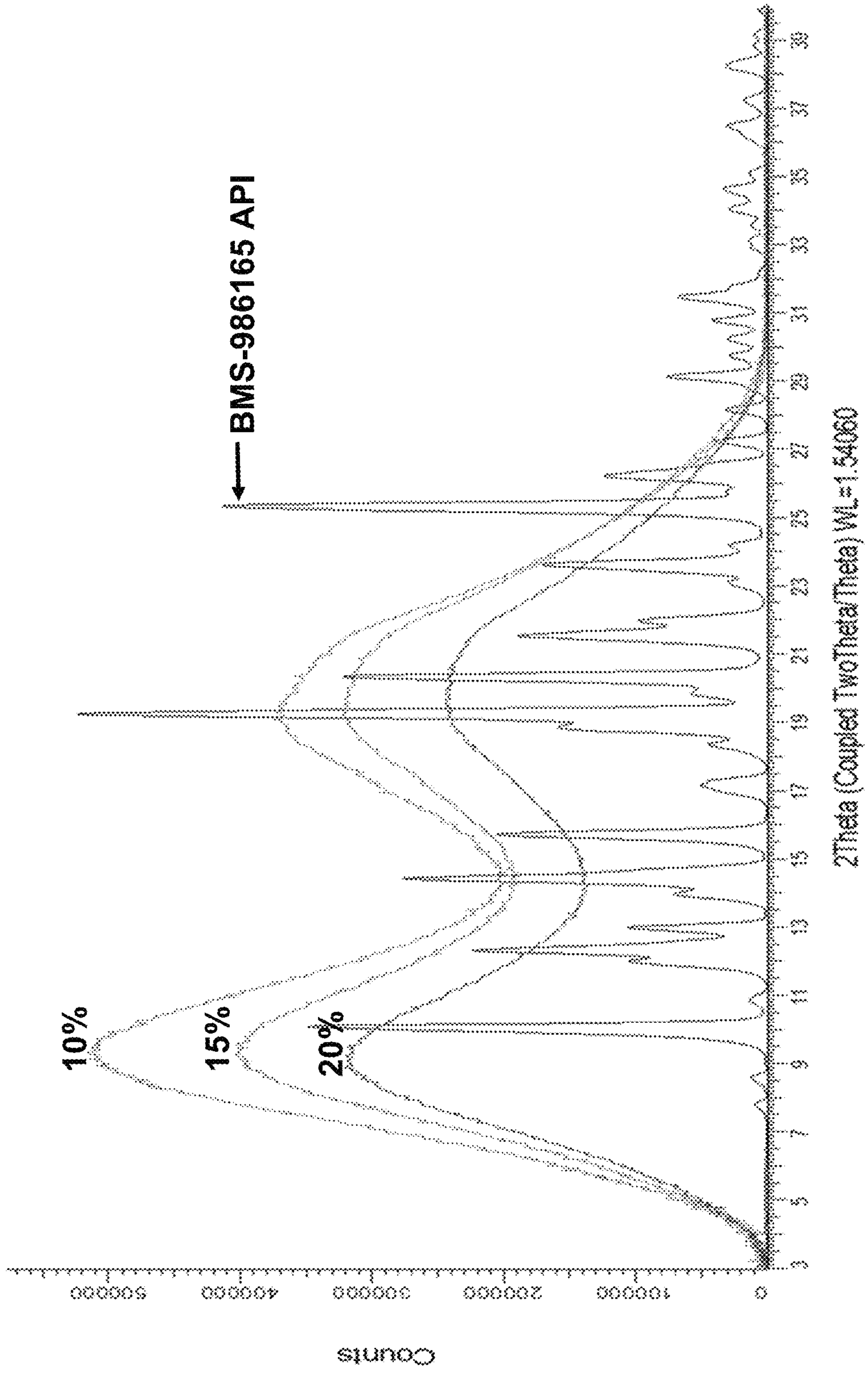
FIGS. 1A and 1B show PXRD diffractograms for 10%, 15%, and 20% BMS-986165:HPMCAS-H SDDs, as described in Example C.

The features and advantages of the present invention may be more readily understood by those of ordinary skill in the art upon reading the following detailed description. It is to be appreciated that certain features of the invention that are described above and below in the context of separate embodiments may also be combined to form a single embodiment. Conversely, various features of the invention that are described in the context of a single embodiment for reasons of brevity may also be combined so as to form sub-combinations thereof.

Formulations and Dosage Forms

The present invention provides oral dosage forms of 6-(cyclopropaneamido)-4-((2-methoxy-3-(1-methyl-1H-1,2,4-triazol-3-yl)phenyl)amino)-N-(methyl-d3)pyridazine-3-carboxamide (BMS-986165) made from dispersions of amorphous BMS-986165. The dispersions generally comprise amorphous BMS-986165 and one or more polymers. The dispersions are used to make various dosage forms for oral administration, including dosage forms providing immediate release of BMS-986165 and dosage forms providing extended release of BMS-986165.

As used herein, "amorphous" refers to a solid form of a molecule and/or ion that is not crystalline. An amorphous solid does not display a definitive X-ray diffraction pattern with sharp maxima; it is a thermodynamically non-equilibrium material that exhibits no long-range periodicity. Compared to BMS-986165 in crystalline form, amorphous BMS-986165 exists in a state of higher energy; amorphous BMS-986165 possesses higher entropy, enthalpy, and Gibbs free energy than crystalline BMS-986165.

A solid amorphous dispersion or amorphous dispersion refers to a dispersion comprising a drug and a polymer, wherein the drug is non-crystalline. An amorphous dispersion of the drug can be prepared by various manufacturing processes such as spray drying, co-precipitation, or hot melt extrusion. A spray-dried dispersion (SDD) is a single-phase, amorphous molecular dispersion of a drug in a polymer matrix; it is an amorphous solid in which the drug is molecularly "dissolved" in a solid matrix. A spray-dried dispersion can be made by dissolving the drug and a polymer in an organic solvent to produce a solution, followed by spray-drying the solution. Techniques for preparing solid dispersions of an amorphous drug in a polymer are disclosed in, for example, U.S. Pat. Nos. 9,095,585 and 9,468,604, the contents of each of which are hereby incorporated by reference in their entirety herein. Solid dispersions are also described in, for example, U.S. Pat. No. 8,263,128.

The absence of crystalline drug in an amorphous dispersion may be characterized by modulated differential scanning calorimetry (mDSC), powder X-ray diffraction (PXRD), near infrared spectroscopy (NIR), or any other standard analytical technique. For example, mDSC assesses the thermal properties of an SDD; for an amorphous SDD, analysis by mDSC will yield a single glass transition temperature. mDSC can also detect crystalline phase separation, as the crystalline phase will show a unique thermal signal. PXRD uses x-rays to identify crystal form in solid powders and can be used to analyze SDDs, for example to confirm an SDD is a single amorphous phase, with no measurable crystalline material.

BMS-986165 crystalline free base exhibits pH-dependent solubility with low solubility at pHs>4. BMS-986165 crystalline free base therefore exhibits pH-dependent absorption in the GI tract. For immediate release formulations, such pH-dependent properties may result in a reduction in bioavailability when dosed with acid reducing agents, such as, e.g., famotidine or omeprazole. While using the HCl salt form of BMS-986165 for immediate release formulations mitigates the pH effect, formulations made with the HCl salt form of BMS-986165 were observed to convert to the free base form of BMS-986165 during stability testing. While using the higher-energy, amorphous free base form of BMS-986165 helps address the above challenges, formulating amorphous BMS-986165 presents other challenges, including ensuring physical stability of the amorphous form during storage, and maintaining supersaturation of the compound during dissolution in the GI tract.

The present invention provides amorphous BMS-986165 dispersion formulations with improved solubility and bioavailability relative to the crystalline free base form of BMS-986165, with acceptable physical and chemical stability. For example, a spray-dried dispersion of amorphous BMS-986165 in a polymer matrix has higher kinetic solubility as compared to BMS-986165 in a crystalline form. The higher solubility of amorphous BMS-986165 in a spray-dried dispersion is advantageous in maintaining bioavailability when dosed with acid-reducing agents and also in delivery to regions of the GI tract such as the colon where water availability is low and/or where no bile salts are present to enhance solubility of the drug. In addition, the polymer in the dispersion limits precipitation of BMS-986165 once the drug is dissolved, and thereby helps maintain a supersaturated solution once the amorphous form of BMS-986165 dissolves. The amorphous BMS-986165 in a spray-dried dispersion also exhibits physical stability—e.g., the compound remains in the amorphous form and exhibits little or no crystallization upon storage.

While dispersing a drug in a polymer may enhance in vivo drug concentration or bioavailability, the amount of polymer that can be used is limited by the total mass requirements of an oral dosage form. In other words, the bioavailability benefits of decreasing the drug-to-polymer ratio (such that the wt % of drug is lower than the wt % of polymer in the formulation) can be offset by the disadvantages associated with using more polymer in an oral dosage form. For example, when delivery of a particular dose in a single tablet or capsule is desired, using a low drug-to-polymer ratio may result in a tablet or capsule with a large total mass that is too large for swallowing. The percent of drug loading must be high enough so that oral dosage forms of an acceptable size, for the desired dosage strengths, can be made. Yet at the same time, dosage forms with a relatively high percent drug loading can be more prone to crystallization of the drug.

The present invention provides formulations and dosage forms comprising dispersions of amorphous BMS-986165, wherein the formulations and dosage forms achieve the desirable properties of bioavailability and stability, while also satisfying the physical requirements of oral dosage forms. For example, the higher solubility of amorphous BMS-986165 in a spray-dried dispersion enhances bioavailability of the drug, including when dosed with medications that raise gastric pH; the amorphous BMS-986165 spray-dried dispersions are also chemically and physically stable upon storage, and they can be formulated in the desired dosage amounts in swallowable dosage forms.

Certain embodiments of the present invention provide a dispersion wherein the w/w % of BMS-986165 (amorphous) to polymer is in the range of from about 3% to about 80% of BMS-986165 and from about 97% to about 20% polymer. Further embodiments provide a dispersion wherein the w/w % of BMS-986165 to polymer is in the range of from about 4% to about 50% of BMS-986165 and from about 96% to about 50% polymer. In still further embodiments, the w/w % of BMS-986165 is in the range of from about 5% to about 25% BMS-986165 and from about 95% to about 75% polymer. Accordingly, some embodiments provide a dispersion wherein the w/w % of BMS-986165 to polymer is about 25% BMS-986165 and about 75% polymer. In other embodiments, the w/w % of BMS-986165 to polymer is about 15% BMS-986165 and about 85% polymer, or about 10% BMS-986165 and about 90% polymer.

Polymeric starting material suitable to form the polymer matrix of the dispersions (e.g., spray-dried dispersions) as described herein include: hydroxypropyl methylcellulose (HPMC; also referred to as hypromellose) such as HPMC E3; hydroxypropyl cellulose (HPC); methylcellulose (MC); hypromellose phthalate (HPMC-P); cellulose acetate phthalate; hydroxypropyl methylcellulose acetate succinate (HPMCAS; also referred to as hypromellose acetate succinate) such as L, M, and H grades of HPMCAS; Eudragit® L100-55; vinylpyrrolidone-vinyl acetate copolymer (copovidone); polyvinyl pyrrolidone (PVP); polymethacrylate-based copolymers; and polyvinylcaprolactam-based copolymers. Preferably, the polymer chosen to form the polymer matrix is HPMCAS, and HPMCAS H-grade is a preferred grade of this polymer.

In certain embodiments, spray drying is used to produce amorphous BMS-986165 dispersed in a polymer matrix, to make a formulation of 6-(cyclopropaneamido)-4-((2-methoxy-3-(1-methyl-1H-1,2,4-triazol-3-yl)phenyl)amino)-N-(methyl-d3)pyridazine-3-carboxamide. The formulation may then be used for immediate release formulations and dosage forms or may be used to make modified or controlled release formulations and dosage forms.

Accordingly, a dispersion according to the present invention may be combined with one or more other excipients. When a granulation processed is used, an excipient may be added prior to granulation (and thereby be intragranular) and/or may be added after granulation (and thereby be extragranular).

For example, the dispersion formulations of the present invention may comprise crystallization inhibitors. Crystallization inhibitors suitable for the formulations as described herein include cellulosic polymers such as HPMC, HPMCAS, and hydroxypropyl cellulose (HPC), and vinyl polymers such as PVP. Examples of crystallization inhibitors suitable particularly for extended release formulations as described herein include hydroxypropyl methylcellulose (HPMC; also referred to as hypromellose) such as HPMC E3; hypromellose phthalate (HPMC-P); hydroxypropyl methylcellulose acetate succinate (HPMCAS; also referred to as hypromellose acetate succinate) such as L, M, and H grades of HPMCAS; Eudragit® L100-55; vinylpyrrolidone-vinyl acetate copolymer (copovidone); and polyvinyl pyrrolidone (PVP). In preferred embodiments, the crystallization inhibitor is HPMCAS. A crystallization inhibitor may be included in the dispersion or may be added outside the dispersion.

Other excipients that may be included in the dispersion formulations described herein include release-controlling materials. For example, a release-controlling polymer may be mixed with or coated onto an amorphous dispersion of BMS-986165 to produce an extended release formulation. One type of extended release dosage form is an oral dosage form (such as a tablet) containing the dispersion mixed with a release-controlling polymer (and other excipients).

Accordingly, the present invention also provides a formulation for extended release of 6-(cyclopropaneamido)-4-((2-methoxy-3-(1-methyl-1H-1,2,4-triazol-3-yl)phenyl)amino)-N-(methyl-d3)pyridazine-3-carboxamide (BMS-986165), the formulation comprising: an internal phase comprising a dispersion (e.g., spray-dried dispersion) of amorphous BMS-986165 in a polymer matrix; and an external phase comprising a release-controlling polymer. The formulation may be in a form suitable for oral administration to a patient, including pills, capsules, tablets, films, syrups, and powders. Preferably, the formulation is in the form of a tablet.

Notwithstanding the advantages of the amorphous drug over the crystalline drug as described above, there are at least two substantial challenges involved in designing an extended release formulation that contains an amorphous BMS-986165 SDD mixed with a release-controlling polymer (and other excipients). First, there may be incomplete release of drug from the extended release formulation, due to the release-controlling polymer in the formulation; such incomplete release can lead, for example, to delivery of an insufficient amount of drug to the patient. Second, crystallization of the drug can occur: within the spray-dried dispersion itself (internal phase); within the extended release formulation but outside the SDD per se (external phase); and/or after being released from the extended release formulation. The present invention addresses the first challenge by providing for extended release formulations in which suitable polymeric material is chosen as the release-controlling polymer and the viscosity of the polymeric material is selected so as to provide for a desired release rate of the drug. As to the second challenge, in order to maintain the benefits of the amorphous form, the present invention provides that a crystallization inhibitor is in the extended release formulation but outside the spray-dried dispersion per se, to reduce or prevent crystallization of the drug. With the present invention, formulations containing amorphous BMS-986165 with tunable release rates and that maintain the benefits of the amorphous form can be provided to the clinic.

Release-controlling polymers that can be used in the extended release formulations described herein include natural polymers, synthetic biodegradable polymers, and synthetic non-biodegradable polymers, as would be readily apparent to one of ordinary skill in the art in light of the present disclosure. Examples of release-controlling polymers include methylcellulose, hydroxypropyl methylcellulose, hydroxypropyl cellulose, carboxymethyl cellulose, sodium carboxymethyl cellulose, ethyl cellulose, sodium alginate, chitosan, gelatin, tragacanth, xanthan, and mixtures of the foregoing. HPMC is a preferred release-controlling polymer for the extended release formulations described herein. When HPMC is selected as the release-controlling polymer, it preferably has a viscosity in a range of from 80 cP to 120000 cP. Polymer viscosity may be measured with a number of different viscometers that are known in the art.

In certain embodiments, the extended release dispersion formulations include one or more crystallization inhibitors. For extended release formulations that have an internal phase and an external phase, the crystallization inhibitor can be provided in the internal phase and/or in the external phase in the formulations. Suitable crystallization inhibitors are discussed above.

Any of the immediate release and extended release formulations of 6-(cyclopropaneamido)-4-((2-methoxy-3-(1-methyl-1H-1,2,4-triazol-3-yl)phenyl)amino)-N-(methyl-d3)pyridazine-3-carboxamide as described herein may include pharmaceutically acceptable excipients so as to make pills, capsules, tablets, films, syrups, and powders, and so on. For example, conventional matrix materials, fillers, diluents, binders, lubricants, and/or preservatives may be included in the formulations. Examples of matrix materials, fillers, or diluents include lactose, mannitol, xylitol, microcrystalline cellulose, calcium diphosphate, dicalcium phosphate, and starch. Examples of binders include methyl cellulose, microcrystalline cellulose, carboxymethylcellulose, gelatin, starch, gums such as guar gum natural and synthetic gums such as acacia, natural sugars such as glucose or beta-lactose, corn sweeteners, and tragacanth or sodium alginate, polyethylene glycol, and the like. Examples of lubricants include magnesium stearate, calcium stearate, stearic acid, sodium oleate, and the like. Examples of preservatives include sulfites (an antioxidant), benzalkonium chloride, methyl paraben, propyl paraben, benzyl alcohol, and sodium benzoate. Coloring agents may also be used.

In certain embodiments, a dispersion of the present invention is made into a tablet that comprises the dispersion in a weight percent range of 10-50%, such as, e.g., 10% w/w, 15% w/w, 20% w/w, or 25% w/w. In some embodiments, at least 15% of the tablet by weight is the dispersion. In certain embodiments, 20% of the tablet by weight is the dispersion.

In further embodiments, the tablet comprises one or more fillers, for example lactose and/or microcrystalline cellulose, in a total weight percent range of 50-80% of the formulation. In some embodiments, the total amount of fillers is at least 60% w/w, and in further embodiments at least 70% w/w of the formulation. In particular embodiments, the dispersion formulation comprises lactose and microcrystalline cellulose that together are at least 70% w/w of the formulation. In further embodiments, the ratio of microcrystalline cellulose:lactose filler is 50:50; in other embodiments, the ratio of microcrystalline cellulose:lactose filler is 70:30.

In certain embodiments, the tablet dosage form of the invention comprises a disintegrant (e.g., crospovidone, croscarmellose, etc.) in a weight percent range of 3-10%, such as, e.g., 5%. In embodiments, the disintegrant is croscarmellose. When a granulation process is used, the disintegrant may be positioned to be intragranular, extragranular, or both. For example, a tablet may contain croscarmellose 5% w/w (50:50 intragranular:extragranular).

In additional embodiments, the tablet dosage form comprises a lubricant, for example magnesium stearate, in a weight percent range of 0.25-2.0%, such as, e.g., 0.25%, 0.5%, or 0.75%.

The phrase "pharmaceutically acceptable" as employed herein refers to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The formulations and dosage forms according to the present invention may contain from about 1 mg to about 100 mg of BMS-986165, or about 1 mg to about 40 mg of BMS-986165, e.g., 3 mg, 6 mg, 12 mg, 15 mg, or 36 mg of BMS-986165. In embodiments, the formulations and dosage forms contain from 12 mg to 36 mg of BMS-986165. In embodiments, a 100 mg tablet contains about 3 mg BMS-986165, a 200 mg tablet contains about 6 mg BMS-986165, and a 400 mg tablet contains about 12 mg BMS-986165. In embodiments, a 300 mg extended release tablet contains 15 mg of BMS-986165, and such a tablet may be administered once daily to a patient.

Synthesis and Manufacturing

BMS-986165 and other amide-substituted heterocyclic compounds useful as modulators of IL-12, IL-23, and/or IFNα responses, methods of making the same, and methods of using the same are disclosed in U.S. Pat. No. 9,505,748 B2, the contents of which are hereby incorporated by reference in their entirety herein. Other methods of synthesizing BMS-986165 are disclosed in U.S. Provisional Patent Application No. 62/478,789 and PCT/US2018/025100 (published as WO 2018/183649), the contents of each of which are hereby incorporated by reference in their entirety herein.

The amorphous dispersions of the present invention may be prepared by hot-melt extrusion, lyophilization, or spray-drying. In certain embodiments, spray drying procedures are used.

Generally, a spray-dried dispersion (SDD) of solid amorphous BMS-986165 molecularly dissolved in a solid polymer matrix may be made by dissolving BMS-986165 and a polymer (such as HPMCAS) in an organic solvent (or in a mixture of solvents such as a mixture of acetone and water) to produce a solution or suspension, followed by spray-drying the solution or suspension. Further description of suitable SDD synthesis steps in accordance with the present invention is set forth in the Examples section herein. Other manufacturing techniques, such as the techniques disclosed in U.S. Pat. No. 9,468,604, may be used to produce a spray-dried dispersion of BMS-986165 in a polymer matrix, and would be readily apparent to one of ordinary skill in the art in light of the present disclosure.

Accordingly, in some embodiments, a process for making a solid dispersion comprises: (1) adding at least the drug and a polymer, to form a solution or suspension, (2) directing the solution or suspension to a spray drying apparatus and atomizing the solution or suspension into droplets in the spray drying apparatus, (3) contacting the droplets with a drying gas, resulting in solidification of particles, and (4) collecting the particles.

The dispersions described herein may be tableted using equipment and procedures available in the art. Tablets may be manufactured by, for example, preparing a powder mixture, granulating or slugging, adding a filler, lubricant and disintegrant, and pressing into tablets. In certain embodiments, tablets of the present invention are made by a dry granulation process. Direct compression processes may also be used to form tablets as described herein.

Several manufacturing parameters can affect the properties of a tablet dosage form. Such parameters include compaction pressure, solid fraction, and target tensile strength. Compaction pressure refers to the compaction force applied, divided by the area to which the force is applied. A tablet's solid fraction indicates how much of the tablet is solid and not porous. Solid fraction (which may be expressed as, solid fraction=1−porosity), can be calculated by dividing the apparent or envelop density of a tablet by the material true density. Generally, applying a greater compaction pressure results in higher solid fractions, and a higher solid fraction generally corresponds to higher tablet strength. Tablet breaking strength refers to the force required to cause the tablet to fracture or break. A tablet's tensile strength is calculated from the tablet's breaking strength and the tablet's dimensions. A tablet dosage form according to the present invention exhibits suitable friability and tensile strength, while still providing desirable dissolution characteristics.

Description of the manufacturing of tablet formulations, including extended release tablet formulations, containing a spray-dried dispersion of amorphous BMS-986165 in a polymer matrix is set forth in the Examples section herein. Other synthesis techniques, such as are disclosed in U.S. Pat. No. 9,713,594, may be used to produce extended release tablet formulations containing a spray-dried dispersion of amorphous BMS-986165 in a polymer matrix, and would be readily apparent to one of ordinary skill in the art in light of the present disclosure.

In some embodiments, a dispersion containing a given percent w/w of drug is used to make tablets of various dosage strengths. For example, a dispersion that is 15% w/w of amorphous BMS-986165 in a polymer matrix may be used to make tablets that contain 1 mg, 3 mg, 6 mg, and/or 12 mg of BMS-986165. Exemplary tablet weights corresponding to each of these dosage strengths of 1 mg, 3 mg, 6 mg, and 12 mg BMS-986165 are: 50 mg, 100 mg, 200 mg, and 400 mg, respectively.

Dissolution

The dispersion formulations and dosage forms made therefrom can be used to provide immediate release and/or modified release of BMS-986165 in the gastrointestinal tract. Such release can be examined using in vitro dissolution assays. Such assays include the gastric-to-intestinal buffer transfer microcentrifuge test, which can be used to measure the drug concentration enhancement provided by the dispersion containing amorphous BMS-986165 relative to the saturation solubility of the crystalline form of the drug. In the microcentrifuge test, the drug is dosed into a microcentrifuge tube containing media having a pH that reflects the pH of a fasted stomach. After 30 minutes of exposure to the gastric media, the sample is transferred into a higher pH media that reflects the pH of the intestine. Drug concentration is then measured at a desired time point or time points (e.g., 90 minutes after first dosing the drug in gastric media). The drug measured may be comprised of free drug, drug in micelles, and/or drug suspended in solution as drug/polymer colloids. The ultracentrifuge test can also be performed at several time points during the microcentrifuge test to determine the species of dissolved drug that are present; the ultracentrifuge test involves a centrifugation step at 300,000×g to remove any colloidal species that may be present, leaving only free drug and drug in micelles. Another dissolution test is the gastric-to-intestinal buffer transfer Pion dissolution test. Other dissolution tests, such as USP method tests and biorelevant dissolution tests that have been described in the literature, can also be used.

In certain embodiments, immediate release refers to release of at least about 80% of the label claim dose within about 60 minutes in conditions simulating the fasted stomach. In some embodiments, at least about 80% of the label claim dose is released by about 30 minutes in conditions simulating the fasted stomach; in further embodiments, at least about 80% of the label claim dose is released by about 15 minutes (e.g., by about 5 minutes, by about 10 minutes) in conditions simulating the fasted stomach. In further embodiments, such release is achieved in conditions simulating gastric-pH elevated conditions.

In some embodiments, it may be desirable to provide modified release of BMS-986165. Accordingly, certain embodiments of the present invention provide dosage forms exhibiting a controlled release of BMS-986165 following oral administration. For example, dosage forms may release the drug during a time period extending to about 2-8 hours following oral administration. In some embodiments, dosage forms may release drug for up to about 24 hours following oral administration. The release rate provided by such dosage forms may be relatively uniform or constant over time, or may vary over time. In additional embodiments, the dosage forms provide delayed release (e.g., enteric release) of the drug. The conditions under which drug is released, and the rate at which drug is released from such modified release dosage forms, can be assessed in dissolution tests such as those tests described above and in the Examples.

Stability

The formulations and dosage forms of the present invention provide for the physical and chemical stability of amorphous BMS-986165 during processing and upon storage. For example, in certain embodiments, the dispersion formulations and dosage forms of the invention exhibit about 10% or less crystallization of the total BMS-986165 after the formulations and dosage forms are stored for at least about one month (e.g., for three months, or for six months) at 40° C./75% RH (relative humidity) in an open (or alternatively in a closed) container. In certain embodiments, the dispersion formulations and dosage forms of the invention exhibit less than about 10% crystallization—such as, e.g., less than about 5% crystallization, less than about 2% crystallization, or less than about 1% crystallization—of BMS-986165 when stored at 40° C./75% RH (relative humidity) in an open (or alternatively in a closed) container for at least about one month. In further embodiments, the dispersion formulations and dosage forms exhibit less than about 10% crystallization—such as, e.g., less than about 5% crystallization, less than about 2% crystallization, or less than about 1% crystallization—of BMS-986165 when stored at 40° C./75% RH in an open (or alternatively in a closed) container for at least about three months, or in some embodiments for at least about six months. The present invention also provides formulations and dosage forms comprising amorphous BMS-986165 wherein the amorphous form exhibits less than about 10% crystallization—such as, e.g., less than about 5% crystallization, less than about 2% crystallization, or less than about 1% crystallization-when the formulations and dosage forms are stored at 50° C./75% RH in an open (or alternatively in a closed) container for at least about one month, for at least about three months, or for at least about six months. In additional embodiments, the dispersion formulations and dosage forms of the invention exhibit less than about 10% crystallization—such as, e.g., less than about 5% crystallization, less than about 2% crystallization, or less than about 1% crystallization—of BMS-986165 when stored at 25° C./60% RH (relative humidity) in an open (or alternatively in a closed) container for at least about one month, for at least about three months, or for at least about six months. Percent crystallization can be assessed by techniques known in the art and described herein (e.g., PXRD, among others).

For example, certain embodiments of the invention provide a dispersion comprising 15% amorphous BMS-986165: 85% HPMCAS-H, wherein the amorphous BMS-986165 remains non-crystalline through six months of storage at 40° C. and 75% relative humidity (in an open container or in a closed container), as determined by PXRD and/or SEM.

Furthermore, in certain embodiments, the BMS-986165 in the dispersions provided herein exhibits less than about 5% degradation, less than about 3% degradation, less than about 2% degradation, or less than about 1% degradation when the dispersions, or dosage forms containing the dispersions, are stored under any of the conditions described above, for a time period of at least about one month to at least about six months.

Bioavailability

For an orally administered drug product, drug absorption generally depends on the rate and extent of release of the drug substance from the drug product, the dissolution or solubilization of the drug substance under physiological conditions of the gastrointestinal tract, and the permeation of the drug across the gastrointestinal membrane. A conventional or standard formulation containing a drug exhibiting poor solubility likely will not achieve sufficient solubilization of the drug for enough of the drug to be absorbed into the bloodstream, such that therapeutic levels of the drug are reached in the bloodstream and target tissue. Although BMS-986165 exhibits poor solubility, the formulations and dosage forms of the present invention achieve desirable levels of solubilization and therefore absorption of the drug, while also providing other desirable attributes (e.g., stability upon storage, swallowability for the dosage forms, etc.).

In some embodiments, administering a dosage form comprising a solid amorphous dispersion of BMS-986165 results in improved bioavailability of BMS-986165 relative to administration of the same dose of BMS-986165 in a dosage form containing a crystalline formulation of the drug. Relative bioavailability of the drug can be tested in vivo in animals or humans using conventional methods for making such a determination.

For example, an in vivo test, such as a crossover study, may be used to determine whether a dosage form provides an enhanced relative bioavailability compared with a control. In an in vivo crossover study a "test composition" is dosed to half a group of test subjects (animals or humans) and, after an appropriate washout period (e.g., one week) the same subjects are dosed with a "control composition" that comprises an equivalent quantity of drug as contained in the "test composition." The other half of the group is dosed with the control composition first, followed by the test composition. The relative bioavailability is measured as the concentration in the blood (serum or plasma) versus time area under the curve (AUC) determined for the test composition divided by the AUC in the blood provided by the control composition. Preferably, this test/control ratio is determined for each subject, and then the ratios are averaged over all subjects in the study. Determinations of AUC can be made by plotting the serum or plasma concentration of drug along the ordinate (y-axis) against time along the abscissa (x-axis). The determination of AUCs is a well-known procedure and is described, for example, in Welling, "Pharmacokinetics Processes and Mathematics," ACS Monograph 185 (1986).

In some embodiments, the relative bioavailability of the test composition (e.g., a dosage form comprising an amorphous dispersion of BMS-986165 as described herein) is at least 1.25 relative to a control composition as described above (the AUC provided by the test composition is at least 1.25-fold the AUC provided by the control composition). In further embodiments, the relative bioavailability of the test composition is at least 2.0 relative to a control composition containing a crystalline form of the drug.

The bioavailability of two formulations or dosage forms can also be compared using in vitro dissolution testing as a proxy for in vivo bioavailability. For example, a gastric-to-intestinal media transfer dissolution test can be used to simulate in vivo conditions in the GI tract and can be used to estimate the amount of free drug provided by a given formulation or dosage form. Other dissolution tests, such as the test described in Example E, may be used.

In certain embodiments, the bioavailability of BMS-986165 provided by the dosage forms described herein is not significantly affected by medications that raise gastric pH such as antacids, H2 receptor antagonists, and proton pump inhibitors. For example, while the administration of a proton pump inhibitor (or other gastric pH-raising agent) can affect gastric pH, the solubility of amorphous BMS-986165 in the dispersions described herein is less prone to a pH-effect compared to the solubility of free base crystalline BMS-986165. Administration of a dosage form comprising a dispersion of amorphous BMS-986165 therefore can provide for bioavailability of BMS-986165 for patients who are also being administered a proton pump inhibitor (or other pH-raising agent). Accordingly, certain embodiments of the invention provide an oral dosage form comprising amorphous BMS-986165 dispersed in a polymer matrix, wherein the bioavailability of BMS-986165 from the oral dosage form changes by no more than 25%, by no more than 20%, by no more than 15%, or by no more than 10%, when a gastric pH-raising agent (e.g., a proton pump inhibitor) is concurrently administered with the dosage form. Concurrent administration in this context refers to a subject receiving both a gastric pH-raising agent (e.g., a proton pump inhibitor) and the dosage form of dispersed amorphous BMS-986165. The agent (e.g., proton pump inhibitor) and the BMS-986165 dosage form may be administered on the same day, or within, for example, 3 days of each other. For instance, the agent (e.g., proton pump inhibitor) could be administered within 3 days, 2 days, or 1 day of, or on the same days as, administration of the BMS-986165 dosage form. Concurrent administration includes all such timings for administration of the gastric pH-raising agent (e.g., proton pump inhibitor) and the BMS-986165 solid dispersion dosage form.

The effect of a gastric pH-raising or an acid-reducing agent (e.g., a proton pump inhibitor) on bioavailability can be assessed by a study in which the BMS-986165 dosage form is administered to a first group of test subjects (animals or humans) who are not also being administered the pH-raising agent, while the same BMS-986165 dosage form is administered to a second group of test subjects, where the subjects in that second group are concurrently being administered the pH-raising agent; following an appropriate washout period the first group is then administered the BMS-986165 dosage form along with the pH-raising agent, while the second group is administered the BMS-986165 dosage form without concurrent administration of the pH-raising agent. Thus each subject will have two AUC values (one AUC obtained when taking the pH-raising or acid-reducing agent, the other AUC obtained when not taking the agent), and these AUC values can be compared for each subject. For example, the ratio of the AUCs for each subject can be obtained, and then the ratios for all subjects in the study can be averaged. In certain embodiments, the average ratio obtained by such method is within the range of 0.75-1.25.

The present invention also provides extended release formulations and dosage forms in which a single administration can provide bioavailability that is similar to the bioavailability provided by an immediate release formulation or dosage form administered multiple times during the day to deliver the same total amount of drug as in the extended release formulation or dosage form. For example, an extended release tablet containing a specific dose of BMS-986165 can be administered to a patient once a day, to provide a pharmacokinetic profile for the drug that is comparable to the pharmacokinetic profile for the drug that is provided by the immediate release tablet administered twice a day.

Methods of Treatment

Auto-immune or auto-inflammatory diseases that may be treated using the dosage forms or formulations described herein include psoriasis (e.g., plaque psoriasis), psoriatic arthritis, lupus, lupus nephritis, Sjögren's syndrome, inflammatory bowel diseases (including ulcerative colitis and Crohn's disease), and ankylosing spondylitis.

The dosage forms may be administered orally. Preferably, the dosage form is a tablet. The tablets may contain from about 1 mg to about 100 mg of the drug (BMS-986165), or about 1 mg to about 40 mg of the drug, e.g., 6 mg, 12 mg, 15 mg, or 36 mg. For example, in certain embodiments, a 300 mg tablet is an extended release dosage form containing 15 mg of drug and is administered once daily for the treatment of psoriasis.

The present invention further provides the use of a spray-dried dispersion of amorphous BMS-986165 in a polymer matrix, in the preparation of a medicament for treating an auto-immune or auto-inflammatory disease such as inflammatory bowel diseases (including ulcerative colitis and Crohn's disease) and psoriasis.

In certain embodiments, the methods of treating an auto-immune or auto-inflammatory disease (e.g., inflammatory bowel diseases (including ulcerative colitis and Crohn's disease) and psoriasis) in a patient comprise: administering to a patient a formulation for extended release of 6-(cyclopropaneamido)-4-((2-methoxy-3-(1-methyl-1H-1,2,4-triazol-3-yl)phenyl)amino)-N-(methyl-d3)pyridazine-3-carboxamide (BMS-986165) comprising (i) an internal phase comprising a spray-dried dispersion of amorphous BMS-986165 in a polymer matrix, and (ii) an external phase comprising a release-controlling polymer.

The invention also provides methods of treating an inflammatory bowel disease or psoriasis in a patient, comprising: administering once daily to a patient a formulation for extended release of 6-(cyclopropaneamido)-4-((2-methoxy-3-(1-methyl-1H-1,2,4-triazol-3-yl)phenyl)amino)-N-(methyl-d3)pyridazine-3-carboxamide (BMS-986165) comprising (i) an internal phase comprising a spray-dried dispersion of amorphous BMS-986165 in a polymer matrix, and (ii) an external phase comprising a release-controlling polymer. The inflammatory bowel disease may be ulcerative colitis or Crohn's disease. The psoriasis may be plaque psoriasis. The formulation is preferably in the form of a tablet.

The invention further provides methods of treating an inflammatory bowel disease or psoriasis in a patient, comprising: orally administering once daily to a patient a formulation for extended release of 6-(cyclopropaneamido)-4-((2-methoxy-3-(1-methyl-1H-1,2,4-triazol-3-yl)phenyl)amino)-N-(methyl-d3)pyridazine-3-carboxamide (BMS-986165) comprising (i) an internal phase comprising a spray-dried dispersion of amorphous BMS-986165 in a polymer matrix, and (ii) an external phase comprising a release-controlling polymer. The inflammatory bowel disease may be ulcerative colitis or Crohn's disease. The psoriasis may be plaque psoriasis. The formulation is preferably in the form of a tablet.

The following examples serve only to illustrate the invention and its practice. The examples are not to be construed as limitations on the scope or spirit of the invention.

EXAMPLES

Example A 6-(cyclopropaneamido)-4-((2-methoxy-3-(1-methyl-1H-1,2,4-triazol-3-yl)phenyl)amino)-N-(methyl-d3)pyridazine-3-carboxamide drug substance and HPMCAS are added to a mixture of acetone and water in a suitable tank and mixed to produce a solution. The solution is spray-dried under a nitrogen atmosphere (nitrogen provides an inert atmosphere during manufacturing). The resultant spray-dried mixture is further dried to provide a spray-dried dispersion (SDD), which can be filled and packaged.

To make dispersion formulations and dosage forms with an extended release profile, the SDD, lactose anhydrous, microcrystalline cellulose, and HPMCAS are blended together, and the blended combination is screened. The screened combination and magnesium stearate are blended, and the result is subjected to dry granulation (slugging/roller compaction process) followed by milling. This further result is blended with additional magnesium stearate, followed by tableting to produce a tablet for extended release of 6-(cyclopropaneamido)-4-((2-methoxy-3-(1-methyl-1H-1,2,4-triazol-3-yl)phenyl)amino)-N-(methyl-d3)pyridazine-3-carboxamide.

Example B

The composition of a spray-drying solution for the production of a spray-dried dispersion of solid amorphous BMS-986165 molecularly dispersed in a solid HPMCAS-H matrix (15% w/w:85% w/w) is set forth below in Table B-1.

TABLE B-1

Compositions of Spray Solution and SDD

| Component | Grade | Spray Solution Composition (wt %) | SDD Composition (mg/g) |
|---|---|---|---|
| BMS-986165 | Pharmacy | 0.95 | 150 |
| HPMCAS-H | NF (National Formulary) | 5.36 | 850 |
| Acetone | NF | 79.64 | 0 (volatile; not present in final dosage form) |
| Purified Water | NF | 14.05 | 0 (volatile; not present in final dosage form) |
| Nitrogen | NF | 0 | 0 (used to provide an inert atmosphere during the manufacturing process) |

Table B-2 below sets forth a process overview for the manufacture of a spray dry dispersion of amorphous BMS-986165:HPMCAS-H (15% w/w:85% w/w) using a lab-scale spray dryer with a 150-kg/hr drying gas capacity.

TABLE B-2

Manufacture of BMS-986165: HPMCAS-H SDD

| | Action | Details | Considerations |
|---|---|---|---|
| 1. | Solvent addition | Acetone Purified Water | Add 85/15 acetone/water to appropriate solution preparation vessel and associated components. Begin agitation. |
| 2. | Polymer addition | HPMCAS-H | Add HPMCAS-H to the solution preparation vessel, using agitation. Mix the solution according to the parameters in Table B3 below. |
| 3. | Active addition | BMS-986165 | Add BMS-986165 to the solution preparation vessel, using agitation. |
| 4. | Heat vessel | Heater | Heat solvent to 45° C. while agitating using a jacketed vessel. Follow the mixing time parameters shown in Table B3 below. |
| 5. | Spray-drying | Laboratory-Scale Spray Dryer with a 150-kg/hr drying-gas flow-rate capacity with 6 foot extension DPH gas disperser Nozzle centering device Pressure nozzle: SK 78-16 (Pencil Point) Product | Use 85/15 acetone/water for start-up and shutdown of the spray dryer. Spray-dry at the specified conditions set forth in Table B4 below. |

TABLE B-2-continued

| Manufacture of BMS-986165: HPMCAS-H SDD | | | |
|---|---|---|---|
| | Action | Details | Considerations |
| | | collection: 6-inch outer diameter (O.D.) cyclone<br>Solution feed filter: 230 μm filter size using Mott filter housing<br>Insulate lines from solution tank to nozzle | |
| 6. | Secondary drying | Convection Tray Dryer | Perform secondary drying at the specified conditions set forth in Table B5 below. |

While Table B-2 provides for the addition of the polymer to the solution preparation vessel prior to the addition of the active (BMS-986165), the active (BMS-986165) may be added to the solution preparation vessel before the polymer is added.

Table B-3 below sets forth the solution-preparation conditions for the 15% BMS-986165:85% HPMCAS-H SDD. The spray-drying conditions used to manufacture the BMS-986165:HPMCAS-H SDD on a laboratory-scale spray dryer with a 150-kg/hr drying-gas flow-rate capacity were divided into four sets: (A) preheating, (B) warm-up, (C) feed-solution processing, and (D) shut down. Table B-4 below provides a summary of the respective targets and target ranges for the four sets of conditions.

TABLE B-3

| Spray Solution Preparation | | | |
|---|---|---|---|
| | Minimum Mixing Time | Desired Solution Temperature | Comments and/or Considerations |
| HPMCAS-H | 30 minutes, after addition of last component | 15-27° C. | Solution may be cloudy due to the polymer, but should be free of undissolved solids. |
| BMS-986165 | 2 hours, after achieving desired solution temperature | 15-27° C. at addition 45° C. (40-50° C.) after heating | Solution may be cloudy due to the polymer, but should be free of undissolved solids after heating. |

TABLE B-4

| Spray-Drying Conditions | | | | | | |
|---|---|---|---|---|---|---|
| | | System Gas Flow (g/min) | Dryer Inlet Temp (° C.) | Dryer Outlet Temp (° C.) | Feed Pressure (psig) | Feed Rate (g/min) |
| PREHEAT | Target | 2000 | 110 | | | |
| | Target Range | 1850-2150 | 90-130 | | | |
| WARM-UP | Target | 2000 | 110 | 45 | 160 | 136 |
| | Target Range | 1850-2150 | 90-130 | 40-50 | 100-260 | 116-146 |
| SOLUTION | Target | 2000 | 110 | 45 | 160 | 145 |
| | Target Range | 1850-2150 | 90-130 | 40-50 | 100-260 | 125-155 |
| SHUT | Target | 2000 | 110 | 45 | 160 | 136 |
| DOWN | Target Range | 1850-2150 | 90-130 | 40-50 | 100-260 | 116-146 |

The target level for residual acetone in the SDD was less than 0.5 wt %. Below-LOQ (limit of quantification) levels of acetone were achieved in a development batch of 15% BMS-986165:85% HPMCAS-H SDD after drying at 40° C./15% RH for 20.5 hours. In addition, a residual acetone versus drying study was performed on two separate development batches. Table B-5 below sets forth the secondary drying conditions.

TABLE B-5

| Secondary Drying Conditions | |
|---|---|
| Condition | Value |
| Bed Depth | <2.5 cm |
| Temperature | 40° C. ± 5° C. |
| Relative Humidity | 15% ± 10% |
| Drying Time | 4 to 20 hours |

Preferred storage conditions for the spray solution and SDD are set forth in Table B-6 below.

TABLE B-6

| Storage Conditions | |
|---|---|
| Item | Conditions |
| Spray solution | Up to two weeks at up to 50° C. |
| SDD | Before secondary drying:<br>Up to two weeks in stainless steel at controlled room temperature<br>After secondary drying:<br>Store at controlled room temperature with desiccant |

Example C

Stability of BMS-986165 SDD Formulations

Lots of 25% w/w BMS-986165 SDD with HPMCAS-H were assessed for physical and chemical stability. The HPMCAS SDD was chemically stable at all conditions but powder X-ray diffraction (PXRD) and modulated differential scanning calorimetry (mDSC) data indicated crystallization after storage for 1 month open at 50° C./75% RH and after storage for 3 months at 40° C./75% RH open. Dissolution performance in the microcentrifuge test was unchanged. There was no evidence of physical instability when the dispersion formulation was stored at 40° C./75% RH closed or 25° C./60% RH open for up to 6 months.

Additional testing was undertaken to determine an API loading level in HPMCAS-H that would provide chemical and physical stability, while still providing a desirable dissolution profile. pH-transfer dissolution testing using a Pion UV probe (pH 2 or pH 6 to pH 6.5) showed that release/sustainment in gastric phase and sustainment in intestinal phase generally improved as API loading was reduced.

Figure 1B:
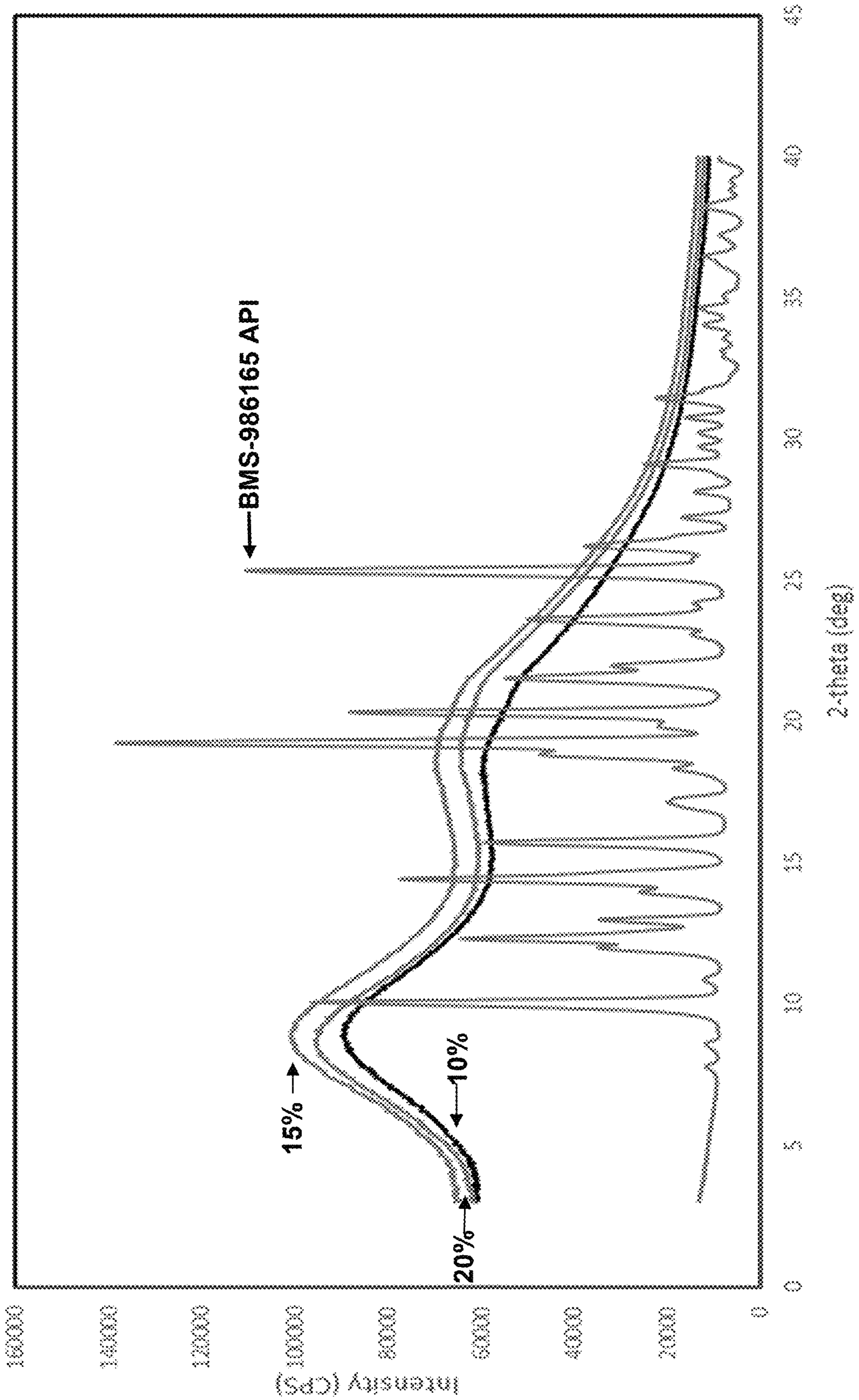
Figure 2A:
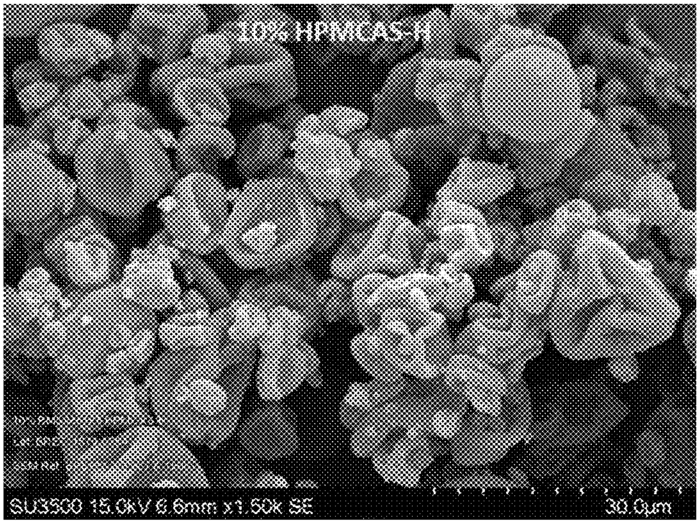
FIGS. 2A-C are SEM images for 10% BMS-986165: HPMCAS-H SDD at 1500× magnification.
Figure 2B:
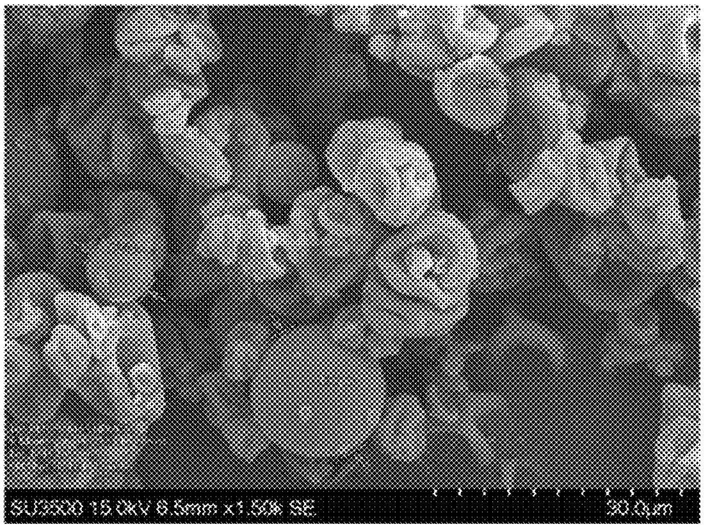
Figure 2C:
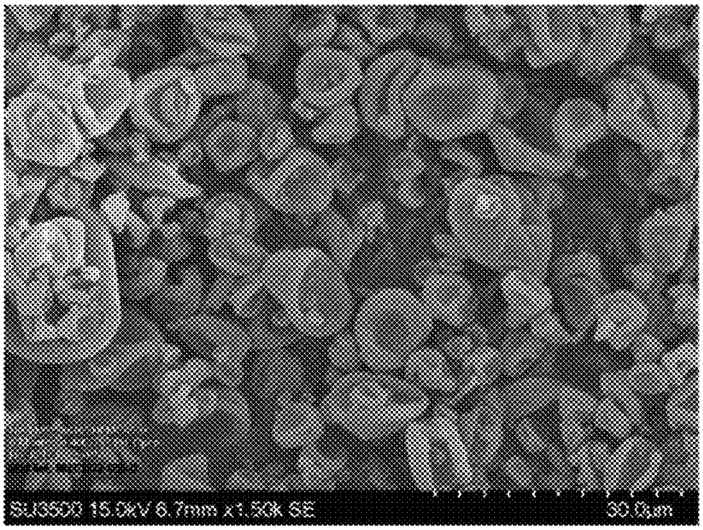
Figure 3A:
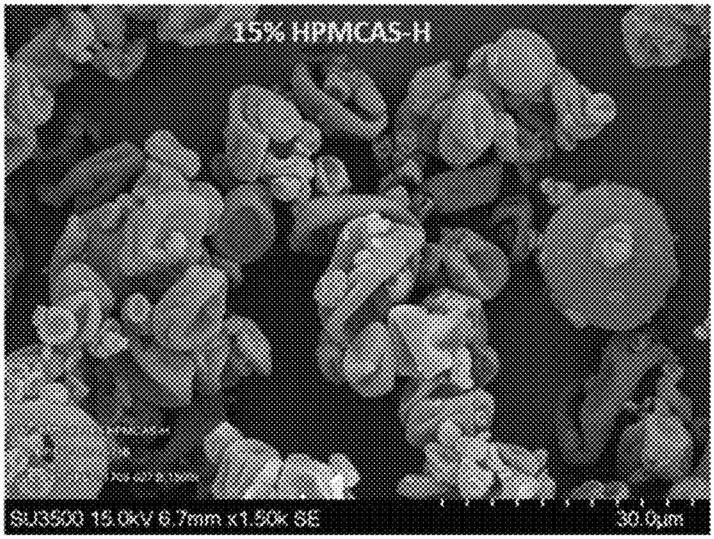
FIGS. 3A-C are SEM images for 15% BMS-986165: HPMCAS-H SDD at 1500× magnification.
Figure 3B:
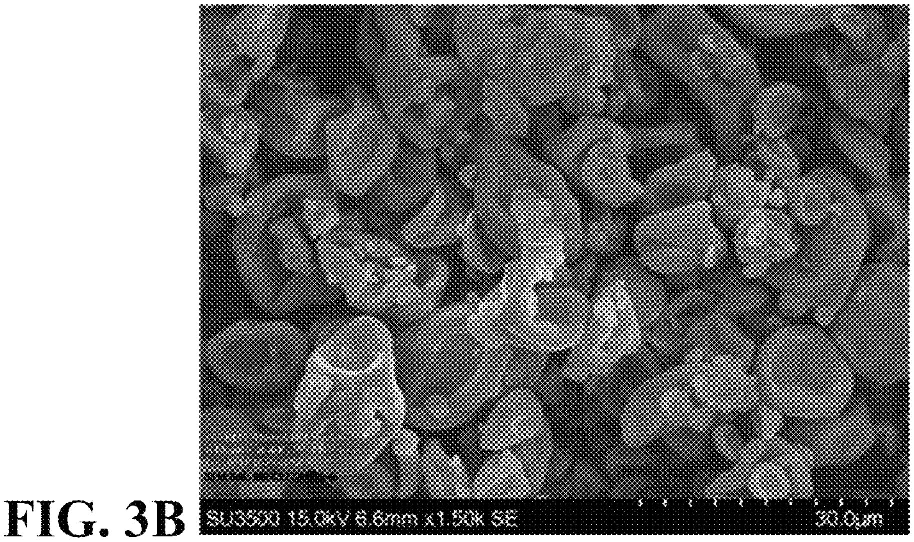
Figure 3C:
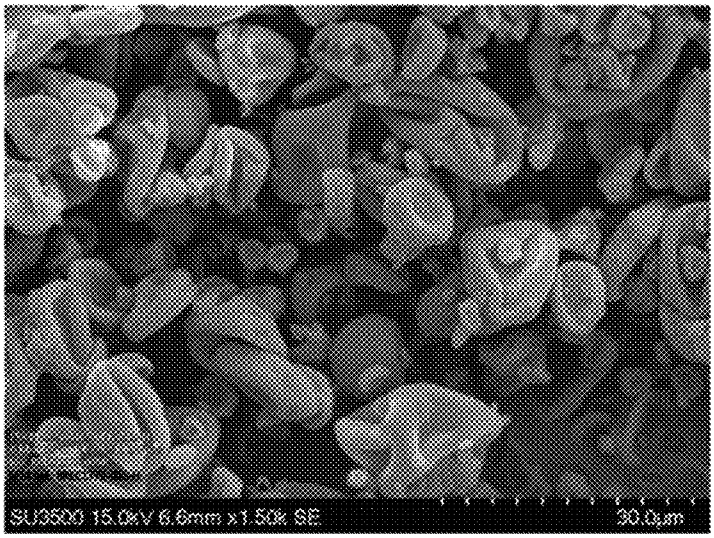
Figure 4A:
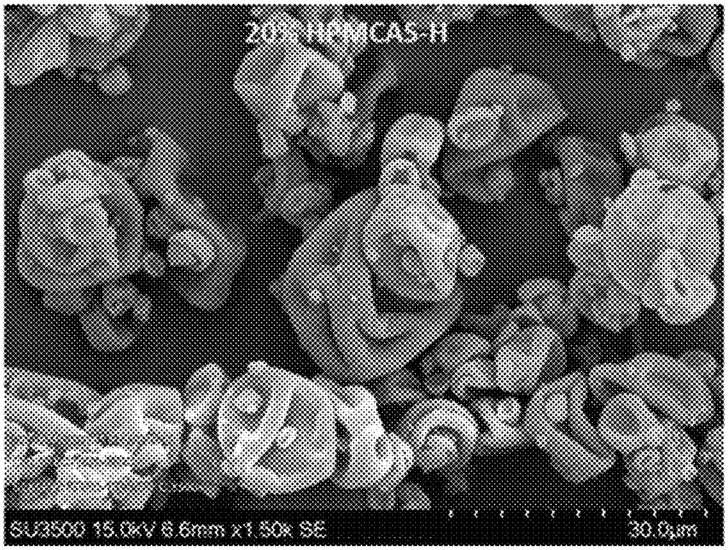
FIGS. 4A-C are SEM images for 20% BMS-986165: HPMCAS-H SDD at 1500× magnification.
Figure 4B:
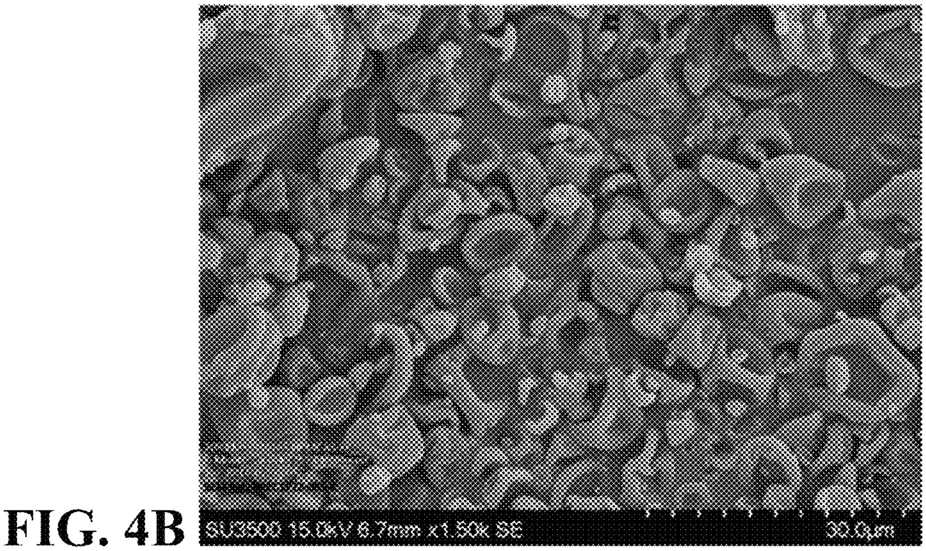
Figure 4C:
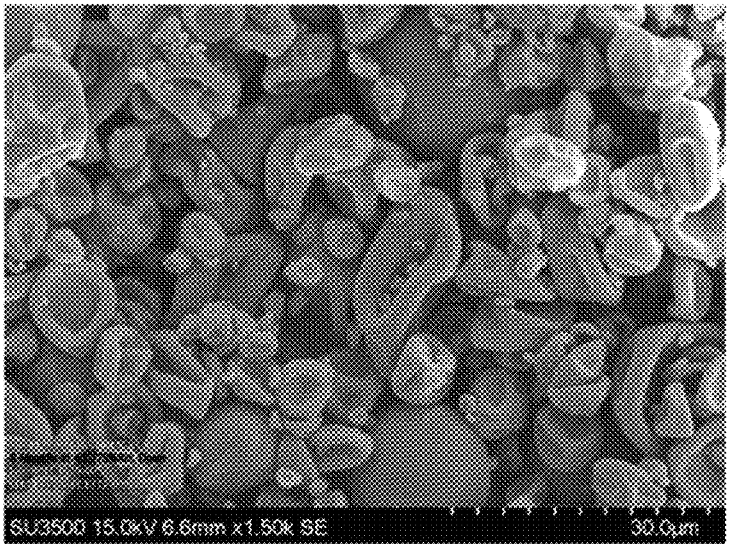

A six-month stability study of SDDs containing 10%, 15% or 20% w/w BMS-986165 in HPMCAS-H showed that all SDDs were chemically stable (Table C). The impurity levels for each SDD matched the ingoing API impurity levels, indicating that the spray drying process did not induce degradation; furthermore, impurity levels did not increase upon storage. There was no evidence of crystallization by PXRD in any SDD after storage for up to 6 months at 40° C./75% RH open (FIG. 1A and FIG. 1). DSC data indicated slight changes similar to those observed in 25% w/w BMS-986165 SDD after exposure to 50° C./75% RH or 40° C./75% RH but there was no trend with API loading and the results were considered to reflect an "ageing" or "annealing" effect rather than crystal formation. Scanning electron microscopy (SEM) images confirmed the presence of a single phase homogenous dispersion (FIG. 2A-C, FIG. 3A-C, FIG. 4A-C).

TAM (thermal activity monitor) experiments using SDDs with BMS-986165 loadings of 10%, 15%, 20%, and 25% (including PXRD on post-TAM samples) confirmed that the physical stability risk was low for HPMCAS-H SDDs containing 20% w/w BMS-986165 or lower. Dissolution performance in the microcentrifuge test was unchanged upon storage.

Lower API loading in SDD, while improving stability, reduces throughput of the spray-drying process; this reduced throughput, however, may be offset by increasing the solids concentration of the spray solution up to a limit of 8% w/w HPMCAS in acetone/water (this limit helps ensure process robustness). The solids concentration is also limited by the solubility of BMS-986165 in acetone/water. To obtain an acceptable throughput at the target spray solution concentration of 1% API, and to ensure sufficient API loading in the SDD such that loading of the SDD in the tablet will still allow tablets of a size suitable for swallowing, an API loading of 15% w/w was selected.

TABLE C

Related Substances of BMS-986165: HPMCAS-H SDDs after 6 months of storage

| | Stability conditions | BMS-986165 | |
|---|---|---|---|
| Retention time (min) | | 11.65 | Total impurities |
| Relative ret. time | | 1.00 | >LOQ |
| API standard | | 99.48 | 0.52 |
| 10% BMS-986165: HPMCAS-H | Initial | 99.51 | 0.49 |
| | 6 months closed, 5° C. | 99.49 | 0.51 |
| | 6 months open, 25° C./60% RH | 99.51 | 0.49 |
| | 6 months closed, 40° C./75% RH | 99.45 | 0.55 |
| | 6 months open, 40° C./75% RH | 99.47 | 0.53 |
| 15% BMS-986165: HPMCAS-H | Initial | 99.51 | 0.49 |
| | 6 months closed, 5° C. | 99.53 | 0.47 |
| | 6 months open, 25° C./60% RH | 99.45 | 0.55 |
| | 6 months closed, 40° C./75% RH | 99.52 | 0.48 |
| | 6 months open, 40° C./75% RH | 99.40 | 0.60 |

TABLE C-continued

Related Substances of BMS-986165: HPMCAS-H SDDs after 6 months of storage

| | Stability conditions | BMS-986165 | |
|---|---|---|---|
| 20% BMS-986165: HPMCAS-H | Initial | 99.55 | 0.45 |
| | 6 months closed, 5° C. | 99.49 | 0.51 |
| | 6 months open, 25° C./60% RH | 99.50 | 0.50 |
| | 6 months closed, 40° C./75% RH | 99.47 | 0.53 |
| | 6 months open, 40° C./75% RH | 99.51 | 0.49 |

Example D

BMS-986165 SDD Tablets

The following formulation was used to make tablets comprising BMS-986165 SDD.

TABLE D

Composition of 3 mg and 12 mg tablets

| Ingredient | % w/w | 3 mg Tablet (mg per tablet) | 12 mg Tablet (mg per tablet) |
|---|---|---|---|
| Intragranular | | | |
| 15:85 BMS-986165-01: HPMCAS-H SDD | 20.00[a] | 20.00[a] | 80[a] |
| Microcrystalline Cellulose | 51.25[b] | 51.25[b] | 205[b] |
| Lactose anhydrous | 22.00 | 22.00 | 88 |
| Croscarmellose Sodium | 2.50 | 2.50 | 10 |
| Silicon Dioxide | 1.00 | 1.00 | 4 |
| Magnesium Stearate | 0.25 | 0.25 | 1 |
| Extragranular | | | |
| Croscarmellose Sodium | 2.50 | 2.50 | 10 |
| Magnesium Stearate | 0.50 | 0.50 | 2 |
| Tablet weight | | 100 mg | 400 mg |
| Tablet size | | 6.35 mm round | 10 mm round |
| Film coating | | | |
| Poly(vinyl alcohol)-based coating A | 4% tablet weight | 4.00 | — |
| Poly(vinyl alcohol)-based coating B | 3% tablet weight | — | 12 |

[a]Assuming SDD is 100% label claim
[b]Amount adjusted to compensate for SDD amount Tablets were manufactured using an Alexanderwerk WP120 roller compaction. Tabletting was performed using a Korsch XL press, and film-coating was conducted using a Thomas Compulab Coater.

The tablets exhibited the desired dissolution/disintegration profiles, appropriate hardness and strength, stability upon storage, and acceptable size for swallowability.

Tablets for a 6 mg dose were also prepared using a 200 mg press weight. For the 6 mg dose, a tablet hardness target of 14 SCU provided appropriate friability (500 drop test) and an acceptable disintegration time of <4 minutes.

Example E

Biorelevant Dissolution of BMS-986165 SDD Tablets and of BMS-986165 HC Salt Capsules (12 mg Strength)

Figure 5:
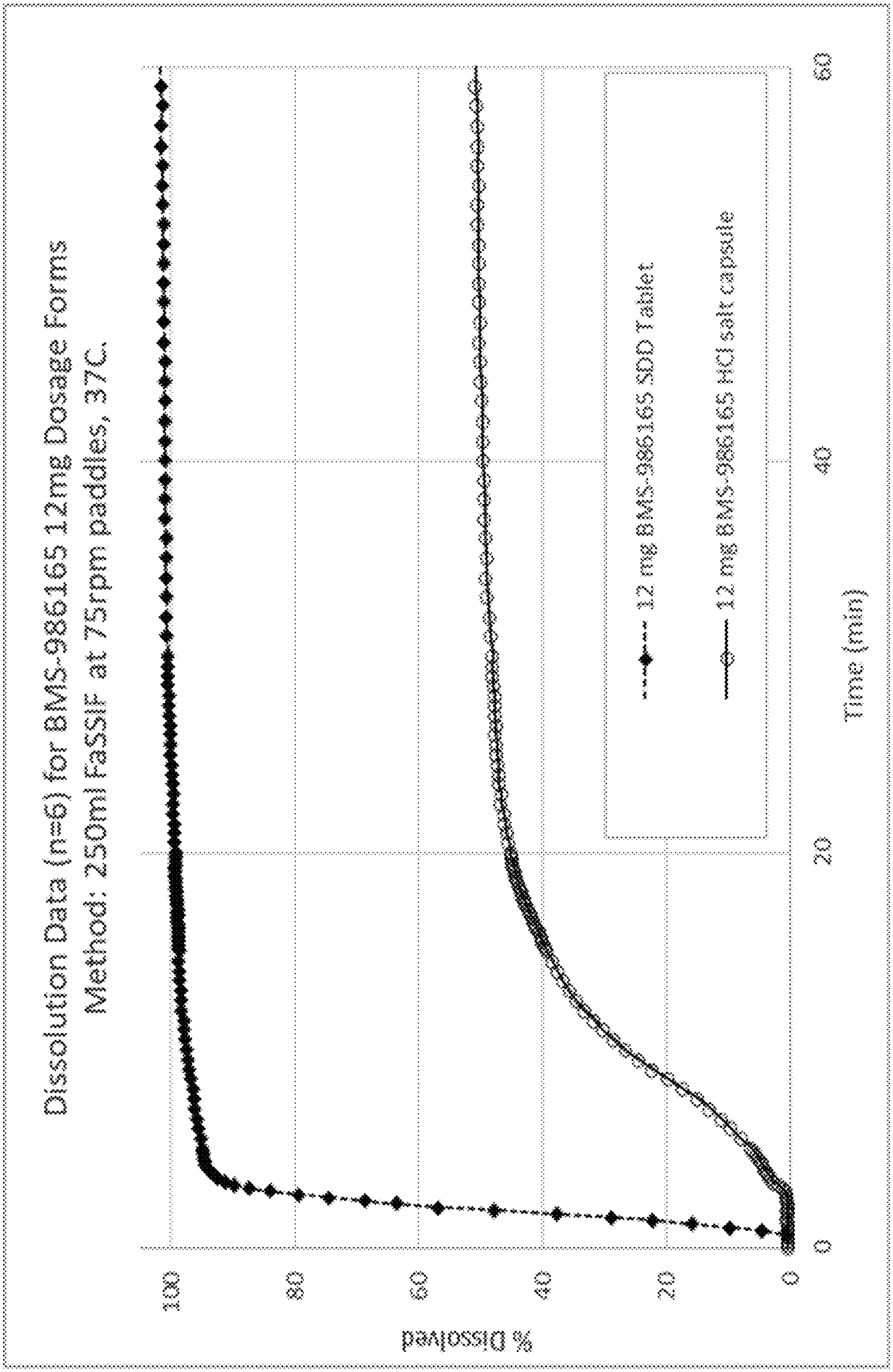
FIG. 5 shows the dissolution profiles for the dosage forms tested as described in Example E.

Dissolution of tablets comprising 15:85 BMS-986165: HPMCAS-H SDD and made by a direct compression process was compared to the dissolution of capsules comprising BMS-986165 HCl salt form (12 mg strength for both dosage forms). Dissolution was examined in biorelevant fasted state simulated intestinal fluid (FaSSIF). Galia et al., Evaluation of Various Dissolution Media for Predicting in vivo Performance of Class I and II Drugs, Pharm Res. 15:698-705 (1998). The recipe for such medium is: pH 6.5; osmolality 270±10 m osmol; sodium taurocholate 3 mM; lecithin 0.75 mM; $KH_2PO_4$ 3.9 grams; KCl 7.7 grams; NaOH qs pH 6.5; deionized water qs 1 liter. The dissolution test was conducted in 250 mL of medium using paddles, at a temperature of 37° C. and a rotation speed of 75 rpm. Six units for each dosage form were tested. FIG. 5 provides the results (mean values (n=6)).

As shown in FIG. 5, the dissolution rate for the SDD tablets was faster than the dissolution rate for the HCl salt capsule when the dosage forms were tested as described above. For the SDD tablets containing amorphous BMS-986165 in a solid dispersion, 95% dissolution was observed by 5 minutes, and 97% dissolution was observed by 10 minutes. For the capsules containing BMS-986165 HCl salt form, 5% dissolution was observed by 5 minutes; 25% dissolution was observed by 10 minutes; 39% dissolution was observed by 15 minutes; and 45% dissolution was observed by 20 minutes.

Dissolution of tablets comprising 15:85 BMS-986165: HPMCAS-H SDD and made by a granulation process was compared to the dissolution of capsules comprising BMS-986165 HCl salt form (12 mg strength for both dosage forms), using the medium and conditions described above (n=6). The results, which are provided in Table E below, show that the dissolution rate for the granulated tablets comprising amorphous BMS-986165 in a solid dispersion is faster than the dissolution rate for the capsules containing BMS-986165 HCl salt form.

TABLE E

| Time in | % Dissolved Mean (Min-Max) [% RSD] n = 6 | |
|---|---|---|
| minutes | Tablet (granulated) | Capsule |
| 10 | 99 (96-100) [1.7] | 27 (23-40) [28.7] |
| 15 | 100 (98-101) [1.2] | 39 (26-50) [20.6] |
| 20 | 100 (99-102) [1.1] | 45 (40-52) [8.7] |
| 30 | 100 (98-102) [1.4] | 48 (46-54) [6.0] |
| 45 | 100 (96-102) [2.1] | 50 (48-55) [5.4] |
| 60 | 100 (100-102) [0.7] | 51 (48-55) [5.1] |

Example F

Crystalline Free Base Extended Release Test (15 mg Strength)

Example 1, Example 2, and Example 3 tablets having the extended release formulations set forth in Table F below were tested. The dissolution testing parameters were as follows: BMS-986165 crystalline free base formulations (Examples 1, 2, or 3) in potassium phosphate buffer (pH 6.8), 20 Mesh Basket, 1000 mL @100 rpm.

TABLE F

| Material | Example 1 | Example 2 | Example 3 |
|---|---|---|---|
| Crystalline BMS-986165 API | 5% | 5% | 5% |
| Methocel K100LV | 30% | — | — |
| Methocel E4M | — | 30% | — |
| Methocel K4M | — | | 30% |
| Anhydrous lactose | 32% | 32% | 32% |
| Microcrystalline cellulose | 32% | 32% | 32% |
| Magnesium stearate | 1% | 1% | 1% |
| Tablet weight | 300 mg | 300 mg | 300 mg |

Figure 6:
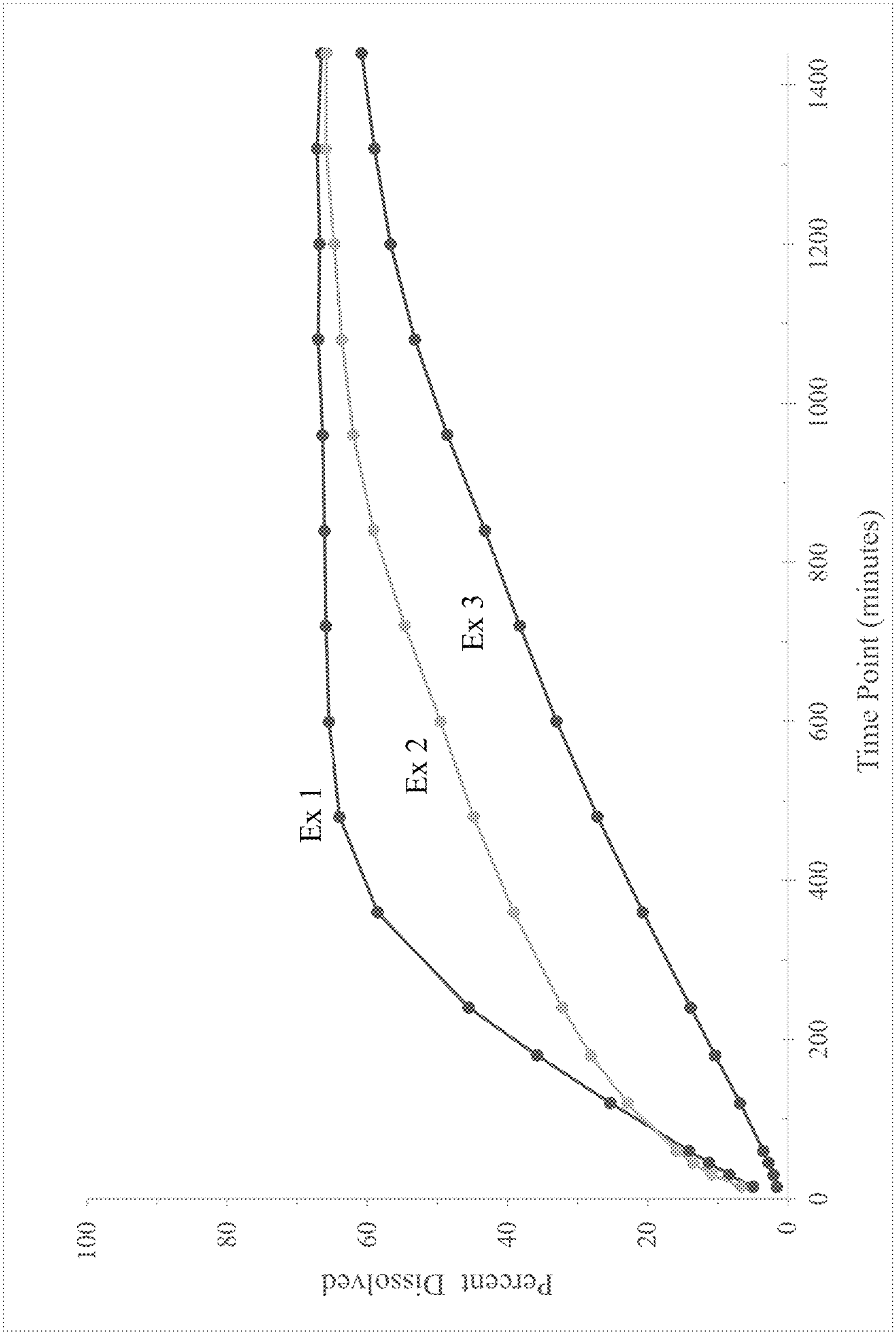
FIG. 6 shows dissolution profiles for extended release formulations of BMS-986165 crystalline free base.

As shown in FIG. 6, the Example 3 formulation had the highest release, 67% after 24 hours, as well as slow release as a result of the relatively high viscosity of the HPMC polymer.

Example G

Extended Release SDD Formulations of BMS-986165

Following the crystalline free base extended release test, the extended release formulations set forth in Table G below were developed.

TABLE G

| Component | Function | Range studied (%) |
|---|---|---|
| BMS-986165-01 SDD (15% BMS-986165-01: 85% HPMCAS) | Active | 11-50% |
| Hypromellose (HPMC) (Viscosity range 80-120000 cP) | Release controlling polymer | 20-30% |
| Lactose anhydrous | Filler | 10-60% |
| Microcrystalline Cellulose | Filler | 10-25% |
| Magnesium Stearate | Lubricant | 1.0% |

"BMS-986165-01" as used in this Example and throughout the present disclosure refers specifically to 6-(cyclopropaneamido)-4-((2-methoxy-3-(1-methyl-1H-1,2,4-triazol-3-yl)phenyl)amino)-N-(methyl-d3)pyridazine-3-carboxamide in free base form. "BMS-986165-01 SDD" as used in this Example and throughout the present disclosure refers to solid amorphous BMS-986165-01 molecularly dispersed in a solid HPMCAS matrix; the BMS-986165-01 is present in the SDD in an amount of 15% by weight of the SDD, and the HPMCAS is present in the SDD in an amount of 85% by weight of the SDD.

Example H

Formulation and Dissolution Profiles for Extended Release SDD Formulations (15 mg Strength)

Example 4, Example 5, and Example 6 tablets having the formulations set forth in Table H below were tested. The dissolution testing parameters were as follows: BMS-986165 SDD formulations (Examples 4, 5, or 6) in potassium phosphate buffer (pH 6.8), 20 Mesh Basket, 1000 mL @100 rpm.

TABLE H

| Material | Example 4 | Example 5 | Example 6 |
|---|---|---|---|
| API | 33.34% | 33.34% | 33.34% |
| Methocel K100LV | 20.00% | — | — |
| Methocel K100M | — | — | 30.00% |
| Methocel K4M | — | 20.00 | — |
| Anhydrous lactose | 45.66% | 22.83% | 35.66% |

TABLE H-continued

| Material | Example 4 | Example 5 | Example 6 |
|---|---|---|---|
| Microcrystalline cellulose | — | 22.83% | — |
| Magnesium stearate | 1.00% | 1.00% | 1.00% |
| Tablet weight | 300 mg | 300 mg | 300 mg |

Figure 7:
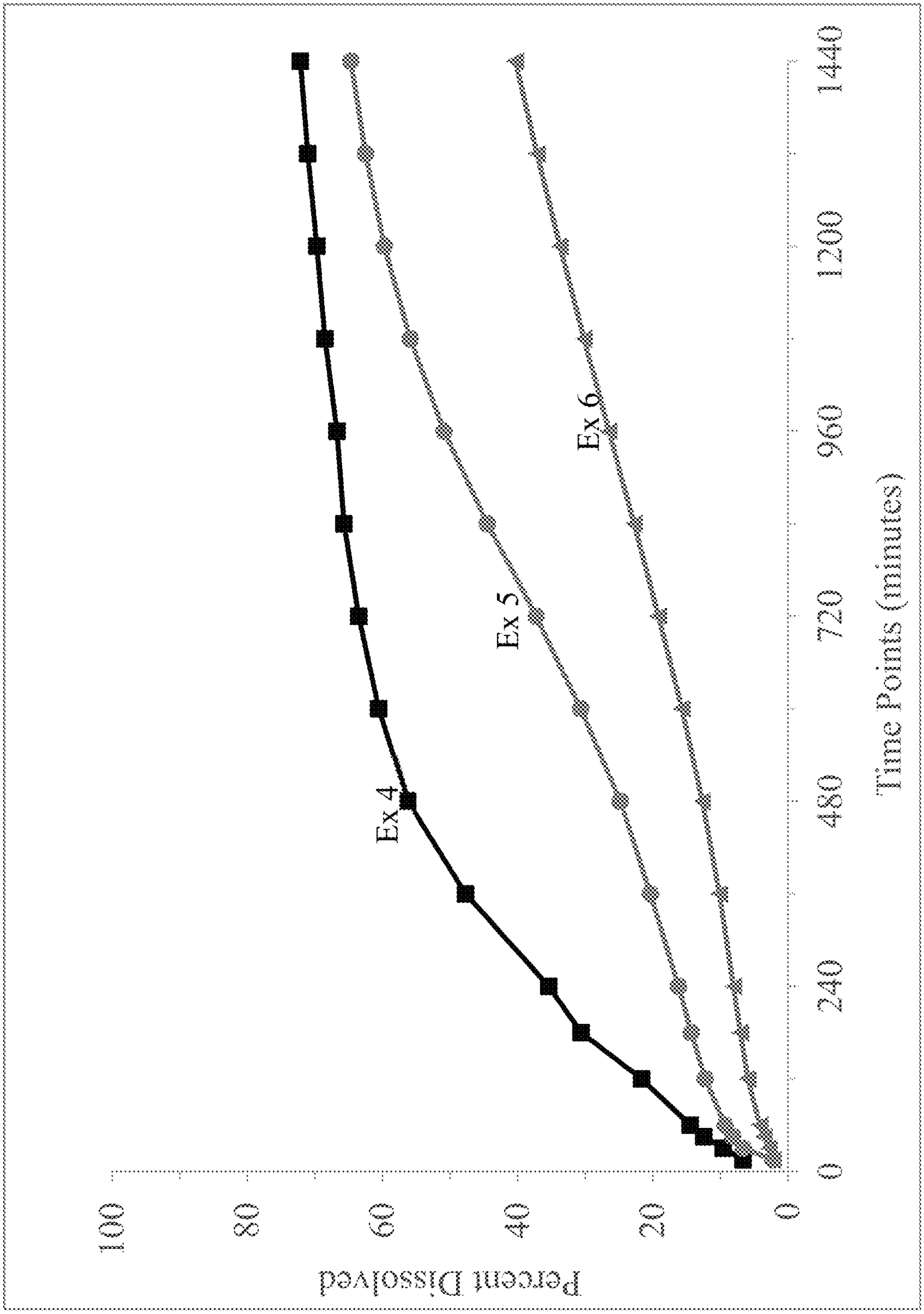
FIG. 7 shows dissolution profiles for extended release spray-dried dispersion formulations of BMS-986165.

By employing an SDD formulation containing amorphous BMS-986165 API, overall drug release at 24 hours was improved (72% for Example 4, as shown in FIG. 7) in comparison with crystalline API (67% for Example 1). However, there was incomplete drug release after 24 hours. This test demonstrated that partial or complete crystallization of drug within or from an SDD formulation can result in negation of the advantages of using an SDD formulation, e.g., by reducing the bioavailability advantage.

Example I

Extended Release SDD Formulations of BMS-986165 with Added HPMCAS Outside SDD Following the above-described SDD formulation test, the extended release formulations set forth in Table I below were developed.

TABLE I

| Component | Function | Range studied (%) |
|---|---|---|
| BMS-986165-01 SDD (15% BMS-986165-01: 85% HPMCAS) | Active | 11-50% |
| Hydroxypropyl Methylcellulose Acetate Succinate (HPMCAS) | Crystallization inhibitor | Up to 16% |
| Hypromellose (HPMC) (Viscosity range 80-120000 cP) | Release controlling polymer | 15-30% |
| Lactose anhydrous | Filler | 10-20% |
| Microcrystalline Cellulose | Filler | 10-20% |
| Magnesium Stearate | Lubricant | 1.0% |

Example J

Formulation and Dissolution Profile for Extended Release SDD Tablet Formulation with Added HPMCAS Outside the SDD Example 7 tablets having the formulation set forth in Table J below were tested. The dissolution testing parameters were as follows: BMS-986165 SDD formulation (Example 7) in potassium phosphate buffer (pH 6.8), 20 Mesh Basket, 1000 mL 100 rpm.

TABLE J

| Material | Example 7 |
|---|---|
| API | 33.34% |
| Methocel K100LV | 20.00% |
| HPMCAS | 15.66% |
| Anhydrous lactose | 15.00% |
| Microcrystalline cellulose | 15.00% |
| Magnesium stearate | 1.00% |
| Tablet weight | 300 mg |

Figure 8:
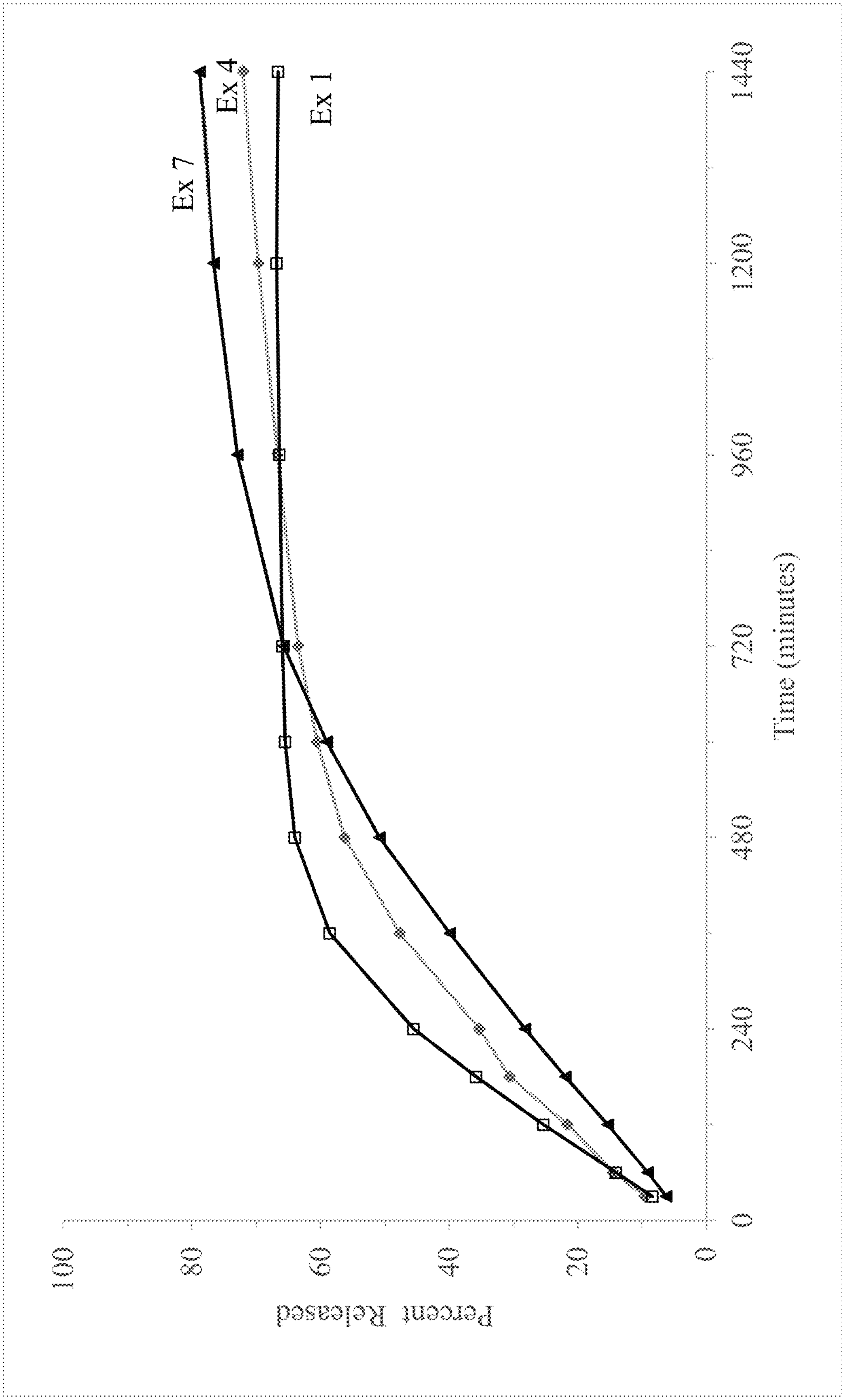
FIG. 8 shows dissolution profiles for extended release spray-dried dispersion formulations of BMS-986165 with added HPMCAS outside the SDD.

The addition of HPMCAS into the formulation—but outside the SDD portion (in the external phase of) the formulation—further increased the overall drug release at 24 hours to 79% (Example 7, as shown in FIG. 8) in comparison to when no additional HPMCAS was part of the formulation (Example 4). This test demonstrated that additional HPMCAS reduced crystallization in the product/system, resulting in increased release of BMS-986165.

Example K

Example 8, Example 9, Example 10, Example 11, and Example 12 tablets having the extended release formulations set forth in Table K below were developed in order to study factors relevant to designing a tunable extended release formulation of BMS-986165. As to viscosity of the release-controlling polymer (HPMC in this case): a range of viscosities was studied by either using a single polymer or mixing polymers of different viscosities. Surface area/volume ratio and dose were studied by changing the tablet weight (dose), thereby also changing the surface area to volume ratio. Different changes can be made to achieve the same surface area to volume ratio.

TABLE K

| Ingredient | % w/w | Ex 8 mg/tab | Ex 9 mg/tab | % w/w | Ex 10 mg/tab | Ex 11 mg/tab | % w/w | Ex 12 mg/tab |
|---|---|---|---|---|---|---|---|---|
| Intra-Granular (IG) | | | | | | | | |
| BMS-986165 SDD | 40.00 | 80.0 | 240.0 | 40.00 | 80.0 | 240.0 | 40.00 | 160.00 |
| HPMCAS | 10.00 | 20.0 | 60.0 | 10.00 | 20.0 | 60.0 | 10.00 | 40.00 |
| Methocel K100LV | 25.00 | 50 | 150 | — | — | — | 5.00 | 20.00 |
| Methocel K15M | — | — | | 25.00 | 50.00 | 150.0 | 20.00 | 80.00 |
| Lactose Anhydrous | 12.00 | 24.0 | 72.0 | 12.00 | 24.0 | 72.0 | 12.00 | 48.00 |
| Microcrystalline cellulose | 12.00 | 24.0 | 72.0 | 12.00 | 24.0 | 72.0 | 12.00 | 48.00 |
| Magnesium stearate | 0.50 | 1.0 | 3.0 | 0.50 | 1.0 | 3.0 | 0.50 | 2.00 |
| Total IG | 99.50 | | | 99.50 | | | 99.50 | |
| Extra-Granular | — | | | — | | | — | |
| Magnesium stearate | 0.50 | 1.0 | 3.0 | 0.50 | 1.0 | 3.0 | 0.50 | 2.00 |
| Total | 100.00 | 200 | 600 | 100.00 | 200 | 600 | 100.00 | 400.00 |
| HPMC viscosity (cP) | 100 | | | 15,000 | | | 8000 | |
| Approx. Surface area to Volume ratio ($in^{-1}$) | | 27 | 16.4 | | 27 | 16.4 | | |

Figure 9:
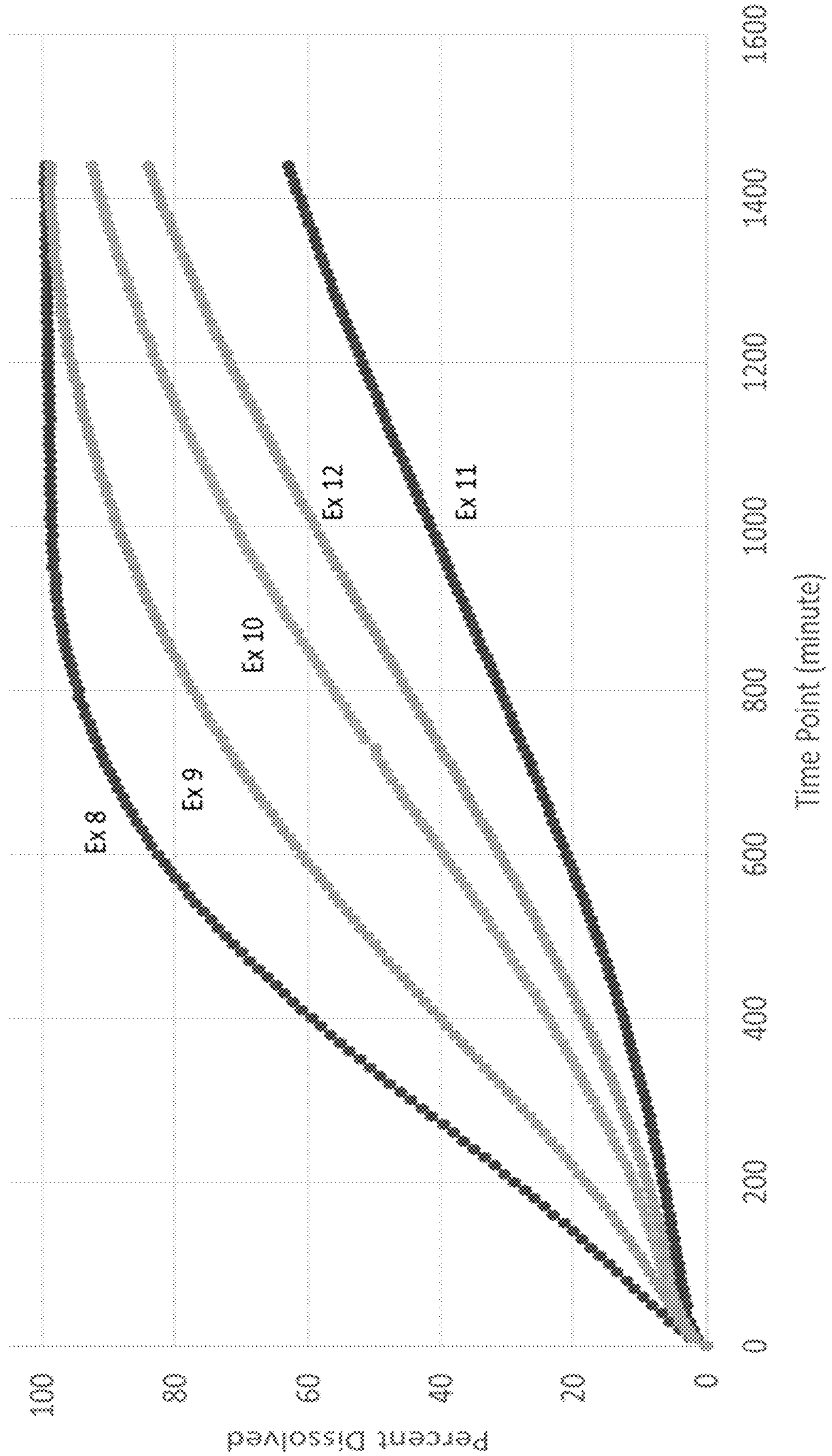
FIG. 9 shows dissolution profiles for extended release spray-dried dispersion formulations of BMS-986165 wherein polymer viscosity, surface area to volume ratio, or both were varied.

FIG. 9 shows the dissolution profiles from varying the viscosity, the surface area to volume ratio, or both. The dissolution testing parameters were as follows: dissolution of the formulations in pH 6.8 phosphate buffer with 1% brij USP II with cage sinker, 1000 mL @75 rpm. As shown in FIG. 9, tunable release (viscosity and surface area/volume) was demonstrated via a range of release profiles, with complete drug release achieved for certain formulations.

Example L

Figure 10:
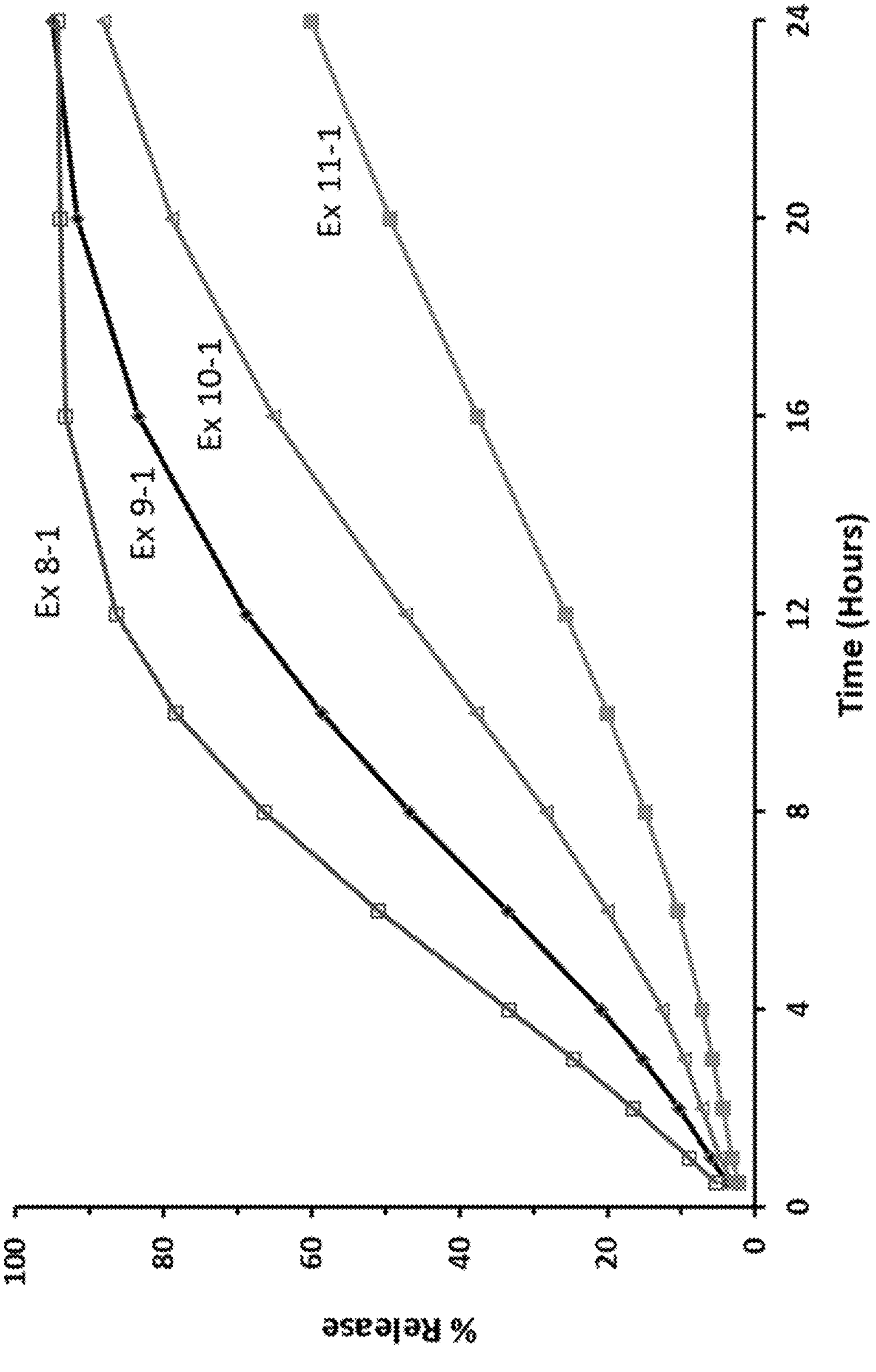
FIG. 10 shows dissolution profiles for extended release spray-dried dispersion formulations of BMS-986165 developed for further clinical study.

Examples 8-1, Example 9-1, Example 10-1, and Example 11-1 tablets having the extended release formulations set forth below in Tables L-1 and L-2 were developed for further clinical study. FIG. 10 shows the dissolution profile for these formulations. The dissolution testing parameters were as follows: BMS-986165 SDD formulations (Examples 8-1, 9-1, 10-1, 11-1) in potassium phosphate buffer (pH 6.8), 1% brij, cage sinker, 1000 mL @75 rpm. Any combination of viscosities and dose as set forth within these four formulations can be used for additional clinical study. Suitable drug dose ranges include a range of 12 mg (200 mg tablet weight) to 36 mg (600 mg tablet weight).

TABLE L-1

| Ingredient | % w/w | Ex 8-1 mg/tab | Ex 9-1 mg/tab |
|---|---|---|---|
| Intra-Granular (IG) | | | |
| BMS-986165 SDD | 40.00 | 80.0 | 240.0 |
| HPMCAS | 10.00 | 20.0 | 60.0 |
| Methocel K100LV | 24.50 | 49.0 | 147.0 |
| Methocel K15M | 0.50 | 1.0 | 3.0 |
| Lactose Anhydrous | 12.00 | 24.0 | 72.0 |
| Microcrystalline cellulose | 12.00 | 24.0 | 72.0 |
| Magnesium stearate | 0.50 | 1.0 | 3.0 |
| Total IG | 99.50 | | |
| Extra-Granular | — | | |
| Magnesium stearate | 0.50 | 1.0 | 3.0 |
| Total | 100.00 | 200 | 600 |

TABLE L-2

| Ingredient | % w/w | Ex 10-1 mg/tab | Ex 11-1 mg/tab |
|---|---|---|---|
| Intra-Granular (IG) | | | |
| BMS-986165 SDD | 40.00 | 80.00 | 240.00 |
| HPMCAS | 10.00 | 20.00 | 60.00 |
| Methocel K100LV | 0.50 | 1.00 | 3.00 |
| Methocel K15M | 24.50 | 49.00 | 147.00 |
| Lactose anhydrous | 12.00 | 24.00 | 72.00 |
| Microcrystalline cellulose | 12.00 | 24.00 | 72.00 |
| Magnesium stearate | 0.50 | 1.00 | 3.00 |
| Total IG | 99.50 | | |
| Extra-Granular | — | | |
| Magnesium stearate | 0.50 | 1.00 | 3.00 |
| Total | 100.00 | 200 | 600 |

Example M

Example 13 and Example 14 tablets with the following formulations for extended release of BMS-986165 were made.

Ex 13

- spray-dried dispersion of amorphous BMS-986165-01: HPMCAS-H (15% w/w: 85% w/w) present in an amount of 40.00% (w/w);
- HPMCAS present in an amount of 10.00% (w/w);
- hypromellose K100 LV Premium CR present in an amount of 0.50% (w/w);
- hypromellose K15M Premium CR present in an amount of 24.50% (w/w);
- lactose anhydrous present in an amount of 12.00% (w/w);
- microcrystalline cellulose present in an amount of 12.00% (w/w); and
- magnesium stearate present in an amount of 1.00% (w/w).

Ex 14

- spray-dried dispersion of amorphous BMS-986165-01: HPMCAS-H (15% w/w: 85% w/w) present in an amount of 40.00% (w/w);
- HPMCAS present in an amount of 10.00% (w/w);
- hypromellose K100 LV Premium CR present in an amount of 24.50% (w/w);
- hypromellose K15M Premium CR present in an amount of 0.50% (w/w);
- lactose anhydrous present in an amount of 12.00% (w/w);
- microcrystalline cellulose present in an amount of 12.00% (w/w); and
- magnesium stearate present in an amount of 1.00% (w/w).

Other combinations of amounts for hypromellose K100 LV and hypromellose K15M can be used, and other premium versions of these hypromellose components that are not CR grade can be used.

Example N

Figure 11A:
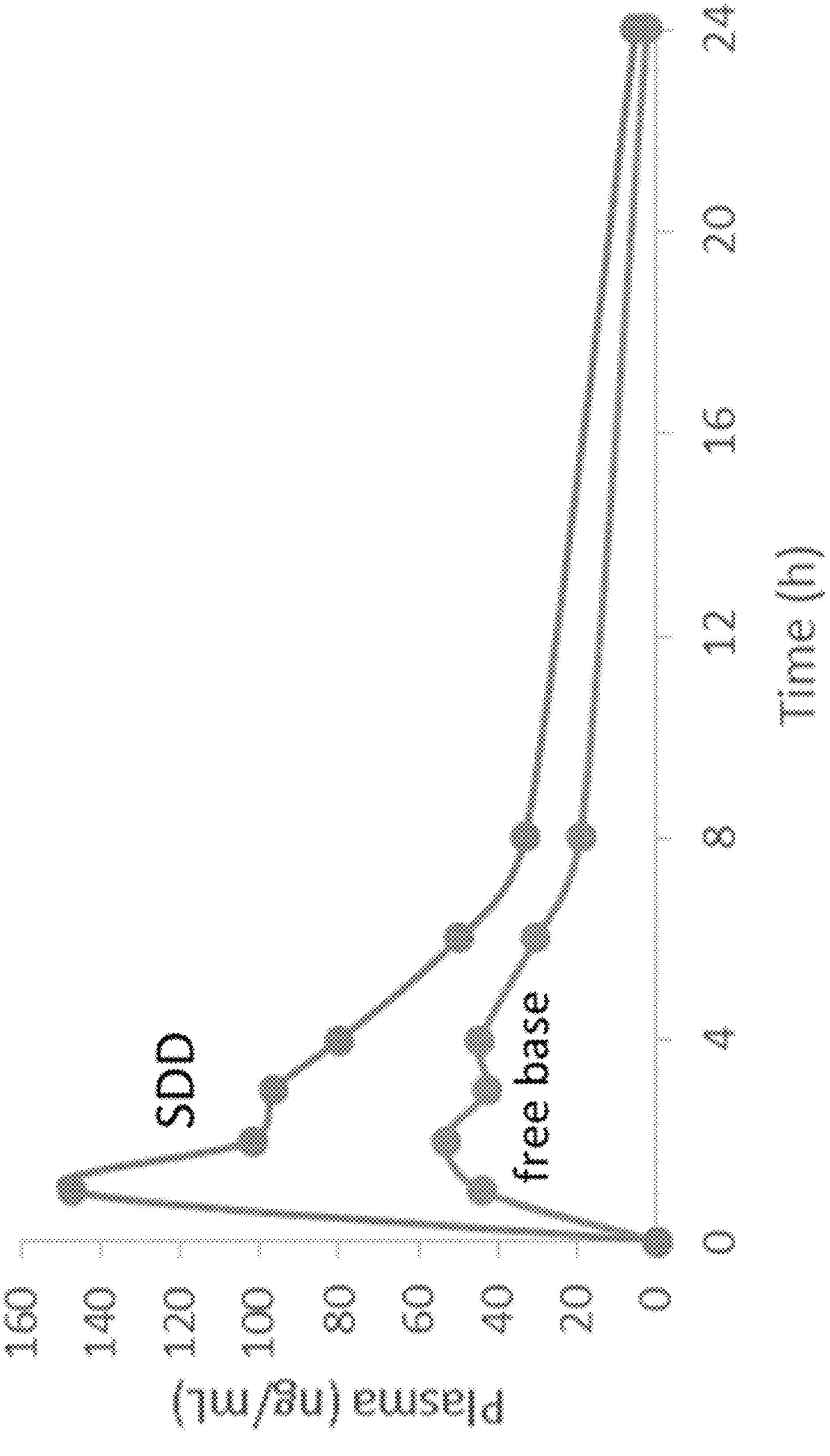
FIG. 11A shows mean plasma-concentration-versus-time curves from a crossover study comparing BMS-986165 SDD tablet to BMS-986165 crystalline free base tablet, in fasted dogs treated with famotidine.
Figure 11B:
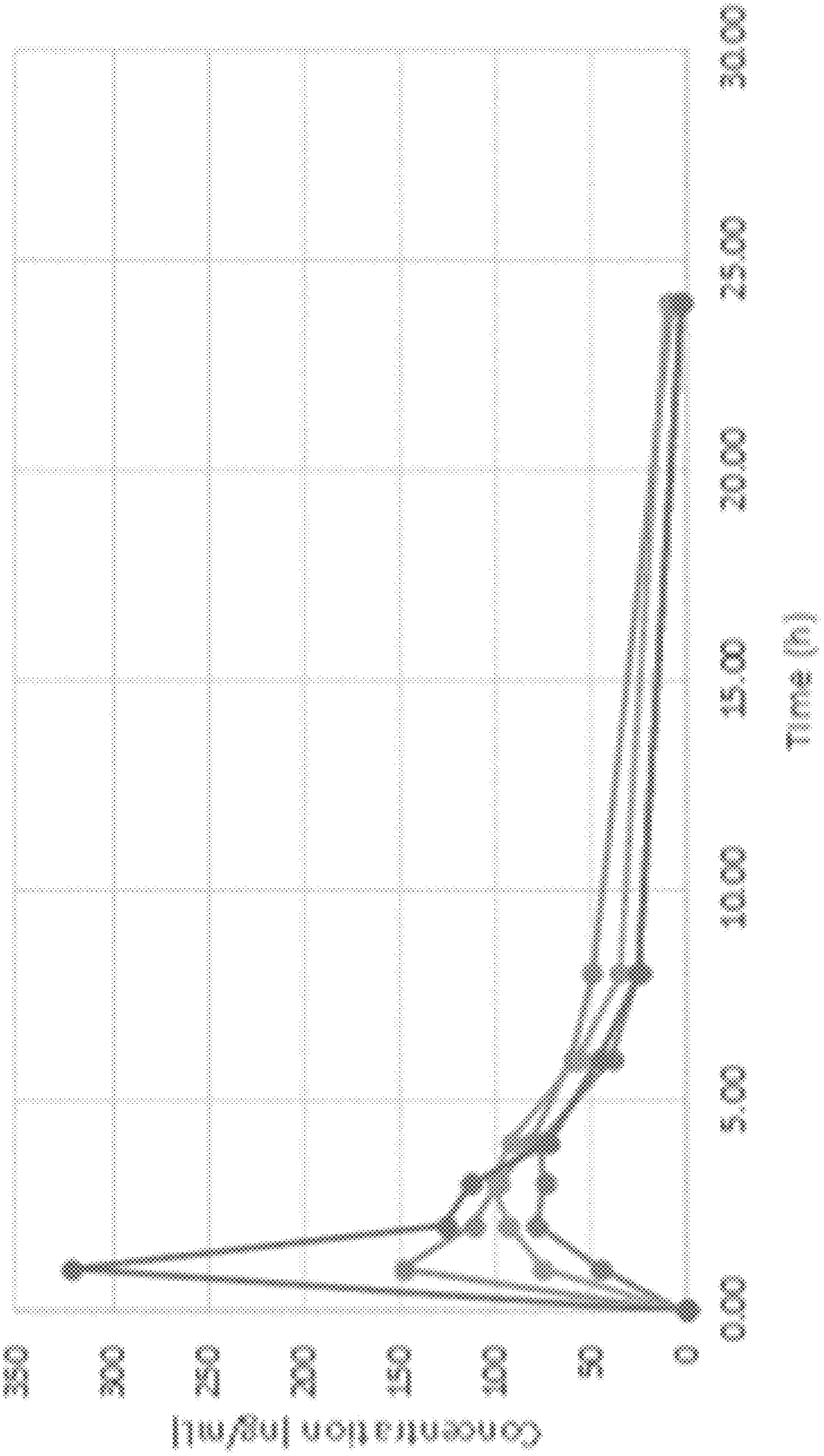
FIGS. 11B and 11C provide the individual plasma-concentration-versus-time curves for each treatment group (n=4).
Figure 11C:
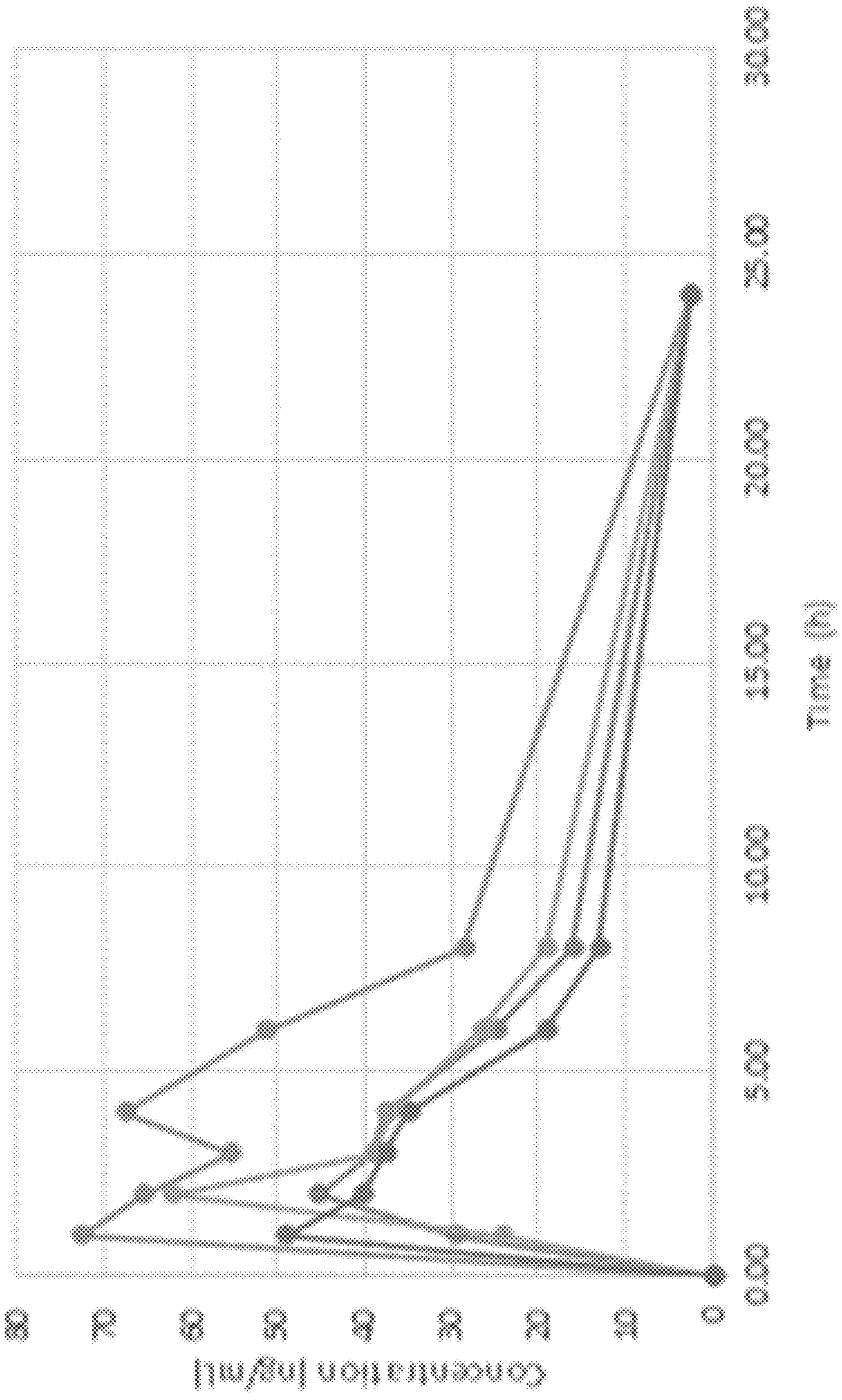

Bioavailability of Tablets Comprising BMS-986165 SDD and of Tablets Comprising BMS-986165 Free Base (Crystalline) in Famotidine-Treated Dogs This study compared the pharmacokinetic profile of tablets comprising BMS-986165-01 SDD (15% BMS 986165-01:85% HPMCAS) to the pharmacokinetic profile of tablets comprising BMS 986165 crystalline free base, in dogs treated with famotidine. The study was a crossover study, with two treatment groups (4 male dogs in each group). For both groups, the dogs were fasted and pretreated with famotidine, which raises gastric pH. Both tablet dosage forms were tested in the 4 mg strength (12 mg human equivalent dose (HED)). Table N-1 and FIGS. 11A-C provide the results.

TABLE N-1

| Pharmacokinetic parameters | | | | | | | | | | | |
|---|---|---|---|---|---|---|---|---|---|---|---|
| | Dose | Cmax (ng/mL) | | Cmin (ng/mL) | | Tmax (h) | $AUC_{0-24h}$ (ng · h/mL) | | BA (%) | | CV |
| | (mg) | Mean | Std Dev | Mean | Std Dev | (Median) | Mean | Std Dev | Mean | Std Dev | (%) |
| SDD tablet, fasted, famo | 4 | 161.83 | 110.04 | 5.39 | 3.65 | 1.5 | 907.99 | 203.12 | 100.00 | n/a | 22.37 |
| Free Base Tablet, fasted, famo | 4 | 57.35 | 12.52 | 2.50 | 0.00 | 1.5 | 462.01 | 145.78 | 50.88 | 16.06 | 31.55 |

As shown in Table N-1, under the elevated gastric-pH condition, tablets comprising BMS-986165 in crystalline free base form exhibited a lower $C_{max}$ and the same median $T_{max}$, compared to tablets comprising amorphous free base BMS-986165 in a solid dispersion. The Area Under the Curve (AUC), calculated from 0 to 24 hours, was also lower for the crystalline free base tablets compared to the SDD tablets; this difference in AUC was statistically significant ($p<0.05$). The variability for both dosage forms was within the variability typically observed for dog pharmacokinetic studies.

These results demonstrate that crystalline free base BMS-986165 tablets exhibit about 50% bioavailability relative to the BMS-986165-01 SDD, at a 4 mg dose (12 mg HED) in the elevated gastric-pH condition.

What is claimed is:

1. A dosage form of 6-(cyclopropaneamido)-4-((2-methoxy-3-(1-methyl-1H-1,2,4-triazol-3-yl)phenyl)amino)-N-(methyl-$d_3$)pyridazine-3-carboxamide (BMS-986165), the dosage form comprising a dispersion of amorphous BMS-986165 dispersed in a polymer matrix;

wherein the proportion of amorphous BMS-986165 to polymer in the dispersion is 4%-50% w/w amorphous BMS-986165 to 96%-50% w/w polymer; and wherein the polymer in the polymer matrix comprises one or more of polymers chosen from:

hydroxypropyl methylcellulose (HPMC), hypromellose phthalate (HPMC-P), hydroxypropyl methylcellulose acetate succinate (HPMCAS), and methacrylic acid-ethyl acrylate copolymer (1:1).

2. The dosage form according to claim 1, wherein the proportion of amorphous BMS-986165 to polymer in the dispersion is 5%-25% w/w amorphous BMS-986165 to 95%-75% w/w polymer.

3. A dosage form of 6-(cyclopropaneamido)-4-((2-methoxy-3-(1-methyl-1H-1,2,4-triazol-3-yl) phenyl) amino)-N-(methyl-d3) pyridazine-3-carboxamide (BMS-986165), the dosage form comprising a dispersion of amorphous BMS-986165 dispersed in a polymer matrix;

wherein the proportion of amorphous BMS-986165 to polymer in the dispersion is 4%-50% w/w amorphous BMS-986165 to 96%-50% w/w polymer; and wherein the polymer in the polymer matrix comprises one or more polymers chosen from:

hydroxypropyl methylcellulose (HPMC), hypromellose phthalate (HPMC-P), and hydroxypropyl methylcellulose acetate succinate (HPMCAS).

4. The dosage form according to claim 3, wherein the polymer in the polymer matrix comprises hydroxypropyl methylcellulose (HPMC).

5. The dosage form according to claim 4, wherein the proportion of amorphous BMS-986165 to polymer in the dispersion is 25% w/w amorphous BMS-986165 to 75% w/w polymer.

6. The dosage form according to claim 4, wherein the HPMC is HPMC E3.

7. The dosage form according to claim 3, wherein the polymer in the polymer matrix comprises hypromellose phthalate (HPMC-P).

8. The dosage form according to claim 1, wherein the BMS-986165 in the dosage form exhibits less than 5% degradation following storage of the dosage form at 40° C./75% Relative Humidity for at least one month.

9. The dosage form according to claim 1, wherein the BMS-986165 in the dosage form exhibits less than 5% crystallization following storage of the dosage form at 40° C./75% Relative Humidity for at least one month.

10. The dosage form according to claim 1, wherein at least 80% of the BMS-986165 in the dosage form is released by 60 minutes after the dosage form is placed in a medium simulating a fasted stomach.

11. The dosage form according to claim 1, wherein at least 80% of the BMS-986165 in the dosage form is released by 30 minutes after the dosage form is placed in a medium having a pH from 1 to 2.

12. The dosage form according to claim 1, wherein the dosage form is an oral dosage form, and bioavailability of BMS-986165 from the oral dosage form is measured by area under the curve of a plasma-concentration-versus-time curve, wherein the bioavailability of BMS-986165 from the oral dosage form administered to a subject concurrently with a gastric pH-raising agent differs by no more than 25% from the bioavailability of BMS-986165 from the oral dosage form administered to the subject without concurrent administration of the gastric pH-raising agent.

13. A dosage form of 6-(cyclopropaneamido)-4-((2-methoxy-3-(1-methyl-1H-1,2,4-triazol-3-yl) phenyl) amino)-N-(methyl-d3) pyridazine-3-carboxamide (BMS-986165), the dosage form comprising a dispersion of amorphous BMS-986165 dispersed in a polymer matrix;

wherein the polymer matrix comprises one or more of:

hydroxypropyl methylcellulose (HPMC), hypromellose phthalate (HPMC-P), hydroxypropyl methylcellulose acetate succinate (HPMCAS), and methacrylic acid-ethyl acrylate copolymer (1:1); and wherein the BMS-986165 in the dosage form exhibits less than 5% degradation following storage of the dosage form at 40° C./75% Relative Humidity for at least one month.

14. A dosage form of 6-(cyclopropaneamido)-4-((2-methoxy-3-(1-methyl-1H-1,2,4-triazol-3-yl) phenyl)

amino)-N-(methyl-$d_3$) pyridazine-3-carboxamide (BMS-986165), the dosage form comprising a dispersion of amorphous BMS-986165 dispersed in a polymer matrix;

wherein the polymer in the polymer matrix comprises one or more polymers chosen from:

hydroxypropyl methylcellulose (HPMC), hypromellose phthalate (HPMC-P), hydroxypropyl methylcellulose acetate succinate (HPMCAS), and methacrylic acid-ethyl acrylate copolymer (1:1); and wherein the BMS-986165 in the dosage form exhibits less than 5% crystallization following storage of the dosage form at 40° C./75% Relative Humidity for at least one month.

15. The dosage form according to claim 14, wherein the proportion of amorphous BMS-986165 to polymer in the dispersion is 5%-25% w/w amorphous BMS-986165 to 95%-75% w/w polymer.

16. The dosage form according to claim 1, wherein the amount of BMS-986165 in the dosage form is from 1 to 12 mg.

17. A method of treating psoriasis in a human subject, the method comprising administering to the human subject the dosage form according to claim 1.

18. The method according to claim 17, wherein the psoriasis is plaque psoriasis.

19. The method according to claim 17, where the amount of BMS-986165 in the dosage form is 6 mg.

20. The method according to claim 17, where the amount of BMS-986165 in the dosage form is 3 mg.

21. A method of treating psoriatic arthritis in a human subject, the method comprising administering to the human subject the dosage form according to claim 1.

22. The method according to claim 21, wherein the amount of BMS-986165 in the dosage form is 6 mg.

23. A method of treating one or more of psoriasis and psoriatic arthritis in a human subject, the method comprising administering to the human subject the dosage form according to claim 2.

24. A method of treating one or more of psoriasis and psoriatic arthritis in a human subject, the method comprising administering to the human subject the dosage form according to claim 3.

25. A method of treating one or more of psoriasis and psoriatic arthritis in a human subject, the method comprising administering to the human subject the dosage form according to claim 14.

26. A method of treating one or more of psoriasis and psoriatic arthritis in a human subject, the method comprising administering to the human subject the dosage form according to claim 15.

27. A method of treating plaque psoriasis in a human subject, the method comprising administering to the human subject the dosage form according to claim 9.

28. A method of treating plaque psoriasis in a human subject, the method comprising administering to the human subject the dosage form according to claim 12.

29. A method of treating plaque psoriasis in a human subject, the method comprising administering to the human subject the dosage form according to claim 13.

* * * * *